(12) United States Patent
Jang et al.

(10) Patent No.: US 11,717,556 B2
(45) Date of Patent: Aug. 8, 2023

(54) STEMNESS-SUPPRESSING COMPOSITION COMPRISING OCT4 FUNCTION-INHIBITING PEPTIDE

(71) Applicant: NATIONAL CANCER CENTER, Goyang-si (KR)

(72) Inventors: Hyonchol Jang, Seoul (KR); Byung Il Lee, Goyang-si (KR); Hong-Duk Youn, Suwon-si (KR); Bomin Song, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 204 days.

(21) Appl. No.: 17/041,926

(22) PCT Filed: Mar. 5, 2019

(86) PCT No.: PCT/KR2019/002527
§ 371 (c)(1),
(2) Date: Sep. 25, 2020

(87) PCT Pub. No.: WO2019/190066
PCT Pub. Date: Oct. 3, 2019

(65) Prior Publication Data
US 2021/0069289 A1 Mar. 11, 2021

(30) Foreign Application Priority Data

Mar. 27, 2018 (KR) .................. 10-2018-0035418
Mar. 4, 2019 (KR) .................. 10-2019-0024944

(51) Int. Cl.
| | |
|---|---|
| *A61K 38/16* | (2006.01) |
| *A61P 35/00* | (2006.01) |
| *A61K 35/28* | (2015.01) |
| *A61K 38/08* | (2019.01) |
| *A61K 38/10* | (2006.01) |
| *A61K 45/06* | (2006.01) |
| *G01N 33/574* | (2006.01) |

(52) U.S. Cl.
CPC ............. *A61K 38/16* (2013.01); *A61K 35/28* (2013.01); *A61K 38/08* (2013.01); *A61K 38/10* (2013.01); *A61K 45/06* (2013.01); *A61P 35/00* (2018.01); *G01N 33/574* (2013.01)

(58) Field of Classification Search
CPC ......... A61K 38/10; A61K 38/16; A61K 38/08
See application file for complete search history.

(56) References Cited

U.S. PATENT DOCUMENTS

2009/0191159 A1* 7/2009 Sakurada .................. A61P 3/10
435/7.1

FOREIGN PATENT DOCUMENTS

| KR | 10-0725314 | 6/2007 | |
|---|---|---|---|
| KR | 10-2014-0043722 | 4/2014 | |
| WO | WO 2009/061837 A1 | 5/2009 | |
| WO | WO-2011038002 A1 * | 3/2011 | ......... A61K 38/1709 |

OTHER PUBLICATIONS

Munyendo et al. "Cell Penetrating Peptides in the Delivery of Biopharmaceuticals", Biomolecules, 2012, 187-202 (Year: 2012).*
International Search Report dated Jun. 24, 2019 in PCT/KR2019/002527 filed on Mar. 5, 2019, 3 pages.
Shin, J. et al., "Aurkb/PP1-mediated resetting of Oct4 during the cell cycle determines the identity of embryonic stem cells," eLIFE, vol. 5, e10877, 2016, pp. 1-21.
Lin, Y. et al., "Reciprocal Regulation of Akt and Oct4 Promotes the Self-Renewal and Survival of Embryonal Carcinoma Cells," Molecular Cell, vol. 48, 2012, pp. 627-640.
Shin, J. et al., "Oct4 resetting by Aurkb-PP1 cell cycle axis determines the identity of mouse embryonic stem ceils," BMB Reports, vol. 49, No. 10, 2016, pp. 527-528.
Malak, P. N. et al., "Novel AKT phosphorylation sites identified in the pluripotency factors OCT4, SOX2 and KLF4," Cell Cycle, vol. 14, No. 23, 2015, pp. 3748-3754.
Lee, et al, "*Arabidopsis* Nuclear-Encoded Plastid Transit Peptides Contain Multiple Sequence Subgroups with Distinctive Chloroplast-Targeting Sequence Motifs", The Plant Cell, vol. 20: 1603-1622, Jun. 2008.

* cited by examiner

*Primary Examiner* — Lianko G Garyu
(74) *Attorney, Agent, or Firm* — Oblon, McClelland, Maier & Neustadt, L.L.P.

(57) ABSTRACT

The present invention relates to a stemness-suppressing composition comprising an OCT4 function-inhibiting peptide and, more particularly, to a composition comprising a peptide as an effective ingredient for suppressing the stemness of various stem cells such as general stem cells, cancer stem cells, and the like, wherein the peptide inhibits the function of OCT4 by inducing the phosphorylation of OCT4. OCT4 function-inhibiting peptides of the present invention are expected to find applications in various fields through the suppressive activity thereof against stemness of stem cells.

6 Claims, 22 Drawing Sheets
Specification includes a Sequence Listing.

| H3-FITC | KDVVRVWFCNRRQKGKRSS |
| H3-1 FITC | KDVVRVWFCN |
| H3-2 FITC | CNRRQKGKRSS |
| H3-3 FITC | VVRVWFCNRRQK |

Cell penetrating peptide (CPP)

Scr	H3-3

Scr	H3-3

SEQUENCE LISTING

<160> NUMBER OF SEQ ID NOS: 19

<210> SEQ ID NO 1
<211> LENGTH: 21
<212> TYPE: DNA
<213> ORGANISM: Artificial Sequence
<220> FEATURE:
<223> OTHER INFORMATION: OCT4 shRNA

<400> SEQUENCE: 1
tcattcacta aggaaggaat t                                            21

<210> SEQ ID NO 2
<211> LENGTH: 21
<212> TYPE: DNA
<213> ORGANISM: Artificial Sequence
<220> FEATURE:
<223> OTHER INFORMATION: PP1 shRNA #1

<400> SEQUENCE: 2
gcgaattatg cgaccaactg a                                            21

<210> SEQ ID NO 3
<211> LENGTH: 23
<212> TYPE: DNA
<213> ORGANISM: Artificial Sequence
<220> FEATURE:
<223> OTHER INFORMATION: PP1 shRNA #2

<400> SEQUENCE: 3
acatttggtg cagaagtggt tct                                          23

<210> SEQ ID NO 4
<211> LENGTH: 150
<212> TYPE: DNA
<213> ORGANISM: Artificial Sequence
<220> FEATURE:
<223> OTHER INFORMATION: Helix 1-3

<400> SEQUENCE: 4
aaccgagtga gaggcaacct ggagaatttg ttcctgcagt gcccgaaacc cacactgcag    60
cagatcagcc acatcgccca gcagcttggg ctcgagaagg atgtggtccg agtgtggttc   120
tgtaaccggc gccagaaggg caagcgatca                                   150

<210> SEQ ID NO 5
<211> LENGTH: 50
<212> TYPE: PRT
<213> ORGANISM: Artificial Sequence
<220> FEATURE:
<223> OTHER INFORMATION: Helix 1-3

<400> SEQUENCE: 5

Asn Arg Val Arg Gly Asn Leu Glu Asn Leu Phe Leu Gln Cys Pro Lys
1               5                   10                  15

Pro Thr Leu Gln Gln Ile Ser His Ile Ala Gln Gln Leu Gly Leu Glu
            20                  25                  30

Lys Asp Val Val Arg Val Trp Phe Cys Asn Arg Arg Gln Lys Gly Lys
        35                  40                  45

Arg Ser
    50

<210> SEQ ID NO 6
<211> LENGTH: 30

```
<212> TYPE: DNA
<213> ORGANISM: Artificial Sequence
<220> FEATURE:
<223> OTHER INFORMATION: Helix 1

<400> SEQUENCE: 6
aaccgagtga gaggcaacct ggagaatttg                                         30

<210> SEQ ID NO 7
<211> LENGTH: 10
<212> TYPE: PRT
<213> ORGANISM: Artificial Sequence
<220> FEATURE:
<223> OTHER INFORMATION: Helix 1

<400> SEQUENCE: 7

Asn Arg Val Arg Gly Asn Leu Glu Asn Leu
1               5                   10

<210> SEQ ID NO 8
<211> LENGTH: 36
<212> TYPE: DNA
<213> ORGANISM: Artificial Sequence
<220> FEATURE:
<223> OTHER INFORMATION: Helix 2

<400> SEQUENCE: 8
ctgcagcaga tcagccacat cgcccagcag cttggg                                  36

<210> SEQ ID NO 9
<211> LENGTH: 12
<212> TYPE: PRT
<213> ORGANISM: Artificial Sequence
<220> FEATURE:
<223> OTHER INFORMATION: Helix 2

<400> SEQUENCE: 9

Leu Gln Gln Ile Ser His Ile Ala Gln Gln Leu Gly
1               5                   10

<210> SEQ ID NO 10
<211> LENGTH: 54
<212> TYPE: DNA
<213> ORGANISM: Artificial Sequence
<220> FEATURE:
<223> OTHER INFORMATION: Helix 3

<400> SEQUENCE: 10
aaggatgtgg tccgagtgtg gttctgtaac cggcgccaga agggcaagcg atca              54

<210> SEQ ID NO 11
<211> LENGTH: 19
<212> TYPE: PRT
<213> ORGANISM: Artificial Sequence
<220> FEATURE:
<223> OTHER INFORMATION: Helix 3

<400> SEQUENCE: 11

Lys Asp Val Val Arg Val Trp Phe Cys Asn Arg Arg Gln Lys Gly Lys
1               5                   10                  15

Arg Ser Ser

<210> SEQ ID NO 12
<211> LENGTH: 42
<212> TYPE: DNA
<213> ORGANISM: Artificial Sequence
```

-continued

```
<220> FEATURE:
<223> OTHER INFORMATION: Helix 3-3

<400> SEQUENCE: 12
gtggtccgag tgtggttctg taaccggcgc cagaagggca ag         42

<210> SEQ ID NO 13
<211> LENGTH: 12
<212> TYPE: PRT
<213> ORGANISM: Artificial Sequence
<220> FEATURE:
<223> OTHER INFORMATION: Helix 3-3

<400> SEQUENCE: 13

Val Val Arg Val Trp Phe Cys Asn Arg Arg Gln Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Helix 3-1

<400> SEQUENCE: 14

Lys Asp Val Val Arg Val Trp Phe Cys Asn
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Helix 3-2

<400> SEQUENCE: 15

Cys Asn Arg Arg Gln Lys Gly Lys Arg Ser Ser
1               5                   10

<210> SEQ ID NO 16
<211> LENGTH: 55
<212> TYPE: PRT
<213> ORGANISM: Mus musculus
<220> FEATURE:
<221> NAME/KEY: MISC_FEATURE
<222> LOCATION: (1)..(55)
<223> OTHER INFORMATION: Mouse OCT4

<400> SEQUENCE: 16

Ile Glu Asn Arg Val Arg Trp Ser Leu Glu Thr Met Phe Leu Lys Cys
1               5                   10                  15

Pro Lys Pro Ser Leu Gln Gln Ile Thr His Ile Ala Asn Gln Leu Gly
            20                  25                  30

Leu Glu Lys Asp Val Val Arg Val Trp Phe Cys Asn Arg Arg Gln Lys
        35                  40                  45

Gly Lys Arg Ser Ser Ile Glu
    50                  55

<210> SEQ ID NO 17
<211> LENGTH: 55
<212> TYPE: PRT
<213> ORGANISM: Homo sapiens
<220> FEATURE:
<221> NAME/KEY: MISC_FEATURE
<222> LOCATION: (1)..(55)
<223> OTHER INFORMATION: Human OCT4
```

```
<400> SEQUENCE: 17

Ile Glu Asn Arg Val Arg Gly Asn Leu Glu Asn Leu Phe Leu Gln Cys
1               5                   10                  15

Pro Lys Pro Thr Leu Gln Gln Ile Ser His Ile Ala Gln Gln Leu Gly
                20                  25                  30

Leu Glu Lys Asp Val Val Arg Val Trp Phe Cys Asn Arg Arg Gln Lys
            35                  40                  45

Gly Lys Arg Ser Ser Ser Asp
        50              55

<210> SEQ ID NO 18
<211> LENGTH: 27
<212> TYPE: PRT
<213> ORGANISM: Artificial Sequence
<220> FEATURE:
<223> OTHER INFORMATION: Cell penetrating peptide CPP Scramble

<400> SEQUENCE: 18

Arg Arg Arg Arg Arg Arg Arg Arg Arg Arg Arg Gly Gly Gly Asp Arg
1               5                   10                  15

Gln Leu Gln Leu Ser Thr Leu Gln Arg Met Leu
                20                  25

<210> SEQ ID NO 19
<211> LENGTH: 26
<212> TYPE: PRT
<213> ORGANISM: Artificial Sequence
<220> FEATURE:
<223> OTHER INFORMATION: Cell penetrating peptide CPP H3-3

<400> SEQUENCE: 19

Arg Arg Arg Arg Arg Arg Arg Arg Arg Arg Arg Gly Gly Gly Val Val
1               5                   10                  15

Arg Val Trp Phe Cys Asn Arg Arg Gln Lys
                20                  25
```

STEMNESS-SUPPRESSING COMPOSITION COMPRISING OCT4 FUNCTION-INHIBITING PEPTIDE

TECHNICAL FIELD

The present invention relates to a composition, a method, a use, and the like, which are capable of suppressing the stemness of various stem cells such as general stem cells and cancer stem cells by comprising a peptide which inhibits the function of OCT4 as an effective ingredient.

This application claims priority to and the benefit of Korean Patent Application Nos. 10-2018-0035418 and 10-2019-0024944 filed in the Korean Intellectual Property Office on Mar. 27, 2018 and Mar. 4, 2019, respectively, and all the contents disclosed in the specifications and drawings of those applications are incorporated in this application.

BACKGROUND ART

Most of the anti-cancer drugs which have been actively developed recently and are practically used for anti-cancer treatment are mostly drugs that target cancer cells which are rapidly proliferating. In the case of anti-cancer treatment using these drugs, cancer cells are effectively killed in the early stage, so that cancer appears to be treated, but ultimately, cancer recurrence and/or metastasis are/is actively occurring because cancer stem cells remaining in the body are not removed, and ultimately, problems of exhibiting resistance to existing anticancer therapies often occur, thus, interest in cancer stem cells has been recently increased. It is known that cancer stem cells as cancer cells having an unlimited regenerative capacity similar to that of general stem cells, proliferate slowly unlike common cancer cells, and have mechanisms different from those of conventionally known cancer cells, as cancer cells having self-renewal or differentiation capabilities which are unique abilities of stem cells. Meanwhile, in the case of stem cell therapeutic agents, which have been actively studied recently, it is difficult to regulate the proliferation, survival, and the like of stem cells, so that side effects caused by this difficulty are occurring. A representative side effect may occur because undifferentiated stem cells remain in the body and become cancerous after the completion of treatment.

Therefore, if there is a method capable of regulating the stemness of stem cells including cancer stem cells, the method is expected to find safe application in various fields of stem cells and effectively suppress the recurrence, metastasis, resistance, and the like of cancer by enhancing the therapeutic effect against cancer.

DISCLOSURE

Technical Problem

The present invention has been devised to solve the problems in the related art as described above, and an object thereof is to provide a composition, a method, a use, and the like, which are capable of suppressing the stemness of various stem cells such as common stem cells and cancer stem cells, which comprise a peptide which inhibits the function of OCT4 as an effective ingredient.

However, a technical problem to be achieved by the present invention is not limited to the aforementioned problem, and the other problems that are not mentioned may be clearly understood by those with ordinary skill in the art from the following description.

Technical Solution

The present invention, for example, a composition, comprises, as an effective ingredient, a peptide comprising one or more amino acid sequences selected from the group consisting of SEQ ID NOS: 5, 7, 9, 11, and 13.

The peptide may also comprise some or all of amino acids of SEQ ID NO: 5, 7, 9, 11, or 13, may comprise the addition, substitution, or deletion of preferably 1 to 10 amino acids, and more preferably, may comprise the addition, substitution, or deletion of 1 to 5 amino acids, and the addition, alteration or replacement may be comprised in front of, behind, or within the peptide, and the peptide is not limited thereto as long as the peptide can suppress the function of OCT4. Further, for the peptide, functional equivalents of one or more amino acid sequences selected from the group consisting of SEQ ID NOS: 5, 7, 9, 11, and 13 are also comprised in the scope of rights of the present invention, and as a result of the addition, substitution, or deletion of amino acid(s), the functional equivalent has a sequence homology of at least 60% or more, preferably 70% or more, more preferably 80% or more, and most preferably 90% or more with the amino acid sequence, and means a peptide exhibiting an activity which is substantially the same as those of one or more amino acid sequences selected from the group consisting of SEQ ID NOS: 5, 7, 9, 11, and 13.

In addition, the peptide may be one in which a polynucleotide comprising one or more base sequences selected from the group consisting of SEQ ID NOS: 4, 6, 8, 10, and 12 is encoded, and a polynucleotide variant may be comprised in the polynucleotide. Specifically, the polynucleotide variant may comprise a base sequence having a sequence homology of 70% or more, more preferably 80% or more, and most preferably 90% or more with one or more base sequences selected from the group consisting of SEQ ID NOS: 4, 6, 8, 10, and 12. For example, the polynucleotide variant comprises a polypeptide having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The "% sequence homology" to a polynucleotide is confirmed by comparing a comparison region with an optimally aligned sequence, and a portion of the polynucleotide sequence in the comparison region may further comprise an addition or deletion (that is, gap) compared to the reference sequence (without addition or deletion) for the optimal alignment of the sequence.

The peptide may be preferably linked to a cell permeable peptide, and various cell permeable peptides known in the art can be used without limitation as long as the cell permeable peptide does not interfere with the OCT4 function-suppressing property of the peptide according to the present invention. In the examples of the present invention, membrane-permeable polyarginine residues (11R) were linked to the end of the peptide. In this case, various methods known in the art may be used while linking a cell permeable peptide, and for example, a linker (GGG and the like), and the like may be comprised, and are not limited thereto.

In an exemplary embodiment of the present invention, the peptide may be characterized by inhibiting the binding between an octamer-binding transcription factor 4 (OCT4) and protein phosphatase 1 (PP1), and more preferably, may be characterized by maintaining the phosphorylation of serine 236 of human OCT4, serine 229 of mouse OCT4, or serine of the corresponding OCT4 of other organisms, but the peptide is not limited thereto as long as the peptide can suppress the function of OCT4.

More specifically, the present invention provides a composition for suppressing the stemness of stem cells, the composition comprising, as an effective ingredient, a peptide comprising one or more amino acid sequences selected from the group consisting of SEQ ID NOS: 5, 7, 9, 11, and 13.

In another exemplary embodiment of the present invention, the peptide may also comprise some or all of amino acids of SEQ ID NOS: 5, 7, 9, 11, or 13, and the peptide may be one in which a polynucleotide comprising some or all of a base sequence of SEQ ID NOS: 4, 6, 8, 10, or 12 is encoded.

In still another exemplary embodiment of the present invention, the stem cells may be selected from embryonic stem cells, germ cells, cancer stem cells, and the like, but are not limited thereto as long as the stem cells are a type of stem cell expressing the OCT4 protein.

In yet another exemplary embodiment of the present invention, the composition may preferably suppress the proliferation, survival, and the like of stem cells by suppressing the stemness of stem cells, and through this, may be used as a method capable of regulating stem cells in all fields using stem cells.

Furthermore, the present invention provides a pharmaceutical composition for preventing or treating cancer, the pharmaceutical composition comprising, as an effective ingredient, a peptide comprising one or more amino acid sequences selected from the group consisting of SEQ ID NOS: 5, 7, 9, 11, and 13.

Further, the present invention provides a method for treating cancer, the method comprising: administering, to an individual, a composition comprising, as an effective ingredient, a peptide comprising one or more amino acid sequences selected from the group consisting of SEQ ID NOS: 5, 7, 9, 11, and 13.

In addition, the present invention provides a use of a composition comprising, as an effective ingredient, a peptide comprising one or more amino acid sequences selected from the group consisting of SEQ ID NOS: 5, 7, 9, 11, and 13 for preventing or treating cancer.

In another exemplary embodiment of the present invention, the peptide may also comprise some or all of amino acids of SEQ ID NOS: 5, 7, 9, 11, or 13, and the peptide may be one in which a polynucleotide comprising some or all of a base sequence of SEQ ID NOS: 4, 6, 8, 10, or 12 is encoded.

In an exemplary embodiment of the present invention, the peptide may be characterized by inhibiting the binding between an octamer-binding transcription factor 4 (OCT4) and protein phosphatase 1 (PP1), and more preferably, may be more preferably characterized by maintaining the phosphorylation of serine 236 of human OCT4 or serine 229 of mouse OCT4, but the peptide is not limited thereto as long as the peptide can suppress the function of OCT4.

In another exemplary embodiment of the present invention, the cancer is preferably thyroid cancer, cervical cancer, brain cancer, lung cancer, ovarian cancer, liver cancer, pancreatic cancer, prostate cancer, skin cancer, tongue cancer, breast cancer, uterine cancer, gastric cancer, rectal cancer, colorectal cancer, blood cancer, and the like, more preferably gastric cancer, colorectal cancer, lung cancer, liver cancer, prostate cancer, thyroid cancer, breast cancer, cervical cancer, ovarian cancer, and the like, but is not limited thereto as long as the cancer is associated with OCT4.

In still another exemplary embodiment of the present invention, the pharmaceutical composition may further comprise an anticancer agent, the anticancer agent may be preferably doxorubicin, cisplatin, gemcitabine, oxaliplatin, 5-FU, and the like, but is not limited thereto.

In yet another exemplary embodiment of the present invention, the pharmaceutical composition preferably suppresses the stemness of cancer stem cells and may suppress the proliferation, survival, metastasis and recurrence of cancer, occurrence of resistance of cancer to anticancer agents, and the like, but the effect is not limited thereto and includes other effects that may be generated by suppressing the stemness of cancer stem cells.

Furthermore, the present invention provides a pharmaceutical composition for preventing or treating cancer, the pharmaceutical composition comprising a peptide which maintains the phosphorylation of serine 236 in an amino acid sequence of OCT4.

Further, the present invention provides a composition for suppressing stemness, the composition comprising a peptide which maintains the phosphorylation serine 236 in an amino acid sequence of OCT4.

In addition, the present invention provides a method for treating cancer, the method comprising: administering, to an individual, a composition comprising a peptide which maintains the phosphorylation of serine 236 in an amino acid sequence of OCT4.

Furthermore, the present invention provides a method for suppressing stemness using a composition comprising a peptide which maintains the phosphorylation of serine 236 in an amino acid sequence of OCT4.

Further, the present invention provides a use of a composition comprising a peptide which maintains the phosphorylation of serine 236 in an amino acid sequence of OCT4 for preventing or treating cancer.

In a specific exemplary embodiment of the present invention, the peptide which maintains the phosphorylation of serine 236 in the amino acid sequence of OCT4 may be a peptide comprising one or more amino acid sequences selected from the group consisting of SEQ ID NOS: 5, 7, 9, 11, and 13.

In addition, the present invention provides a cell therapeutic agent comprising, as effective ingredients, a peptide comprising one or more amino acid sequences selected from the group consisting of SEQ ID NOS: 5, 7, 9, 11, and 13, and stem cells for cell therapy.

In another specific exemplary embodiment of the present invention, the cell therapeutic agent may also regulate stem cells by suppressing the metastasis and survival of therapeutic stem cells and may also suppress the occurrence of cancer due to therapeutic stem cells remaining after treatment becoming cancerous, but the effect is not limited thereto and includes other effects induced by suppressing the function of OCT4.

Furthermore, the present invention provides a method for screening an anticancer agent, the method comprising the following steps: a) treating cells expressing human OCT4 with protein phosphatase 1 (PP1) and a candidate material; b) confirming whether serine 236 in the amino acid sequence of human OCT4 is phosphorylated; and c) selecting the candidate material as an anticancer agent when the phosphorylation of serine 236 is maintained.

Further, the present invention provides a method for screening an anticancer agent, the method including the following steps: a) binding a fluorescent material to a peptide including one or more amino acid sequences selected from the group consisting of SEQ ID NOS: 5, 7, 9, 11, and 13; b) treating and reacting the fluorescent material-bound peptide with protein phosphatase 1 (PP1) and a candidate material; and c) selecting a candidate material with a reduced fluorescence value by measuring a fluorescence polarization value, as an anticancer agent.

The candidate material is not limited as long as the candidate material is a material which can be used as an anticancer agent, such as a nucleotide, DNA, RNA, an amino acid, an aptamer, a protein, a compound, a natural product, and a natural extract.

In addition, the present invention provides a method for suppressing the stemness of stem cells, the method comprising: administering, to an individual, a composition comprising, as an effective ingredient, a peptide comprising one or more amino acid sequences selected from the group consisting of SEQ ID NOS: 5, 7, 9, 11, and 13.

Furthermore, the present invention provides a use of a composition comprising, as an effective ingredient, a peptide comprising one or more amino acid sequences selected from the group consisting of SEQ ID NOS: 5, 7, 9, 11, and 13 for suppressing the stemness of stem cells.

Further, the present invention provides a method for treating cancer, the method comprising: administering, to an individual, a composition comprising, as an effective ingredient, a peptide comprising one or more amino acid sequences selected from the group consisting of SEQ ID NOS: 5, 7, 9, 11, and 13.

In addition, the present invention provides a use of a composition comprising, as an effective ingredient, a peptide comprising one or more amino acid sequences selected from the group consisting of SEQ ID NOS: 5, 7, 9, 11, and 13 for preventing or treating cancer.

Furthermore, the present invention provides a method for suppressing the stemness of stem cells, the method comprising: administering, to an individual, a composition comprising, as an effective ingredient, a peptide which maintains the phosphorylation of serine 236 in an amino acid sequence of human OCT4.

Further, the present invention provides a use of a composition comprising, as an effective ingredient, a peptide which maintains the phosphorylation of serine 236 in an amino acid sequence of human OCT4 for suppressing the stemness of stem cells.

In addition, the present invention provides a method for treating cancer, the method comprising: administering, to an individual, a composition comprising, as an effective ingredient, a peptide which maintains the phosphorylation of serine 236 in an amino acid sequence of human OCT4.

Furthermore, the present invention provides a use of a composition comprising, as an effective ingredient, a peptide which maintains the phosphorylation of serine 236 in an amino acid sequence of human OCT4 for preventing or treating cancer.

Advantageous Effects

Since the peptides for suppressing the function of OCT4 according to the present invention can effectively reduce the stemness of various stem cells, the peptides can be effectively used for suppressing the proliferation of cancer, the recurrence of cancer, the occurrence of resistance of cancer to anticancer agents, and the like, and can also reduce the stemness of general stem cells, so that it is possible to shorten the time and enhance the efficiency in the differentiation of embryonic stem cells into specific cells. Further, in cell therapy using embryonic stem cells, when the composition of the present invention is used, it is possible to completely remove undifferentiated embryonic stem cells remaining after treatment, and accordingly, it is possible to effectively suppress side effects of the occurrence of cancer, so that the stability of cell therapy using embryonic stem cells can be remarkably enhanced.

MODES OF THE INVENTION

Figure 1:
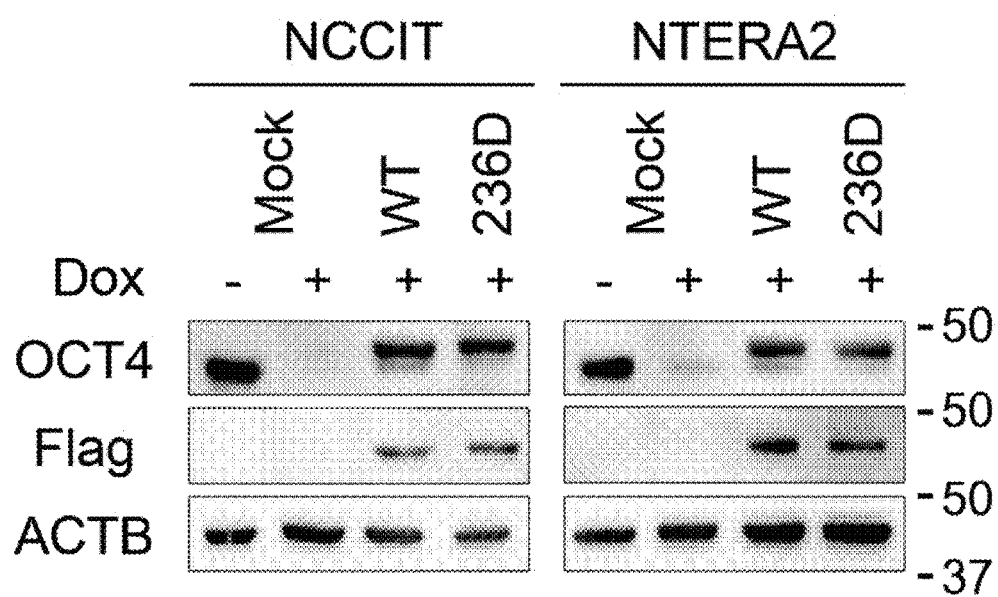
FIG. 1 is a view illustrating the results of confirming transformed cell lines according to an exemplary embodiment of the present invention using western blotting.

The main cause of cancer death is cancer metastasis and treatment resistance, and the fact that the fundamental cause thereof is cancer cells having stemness has been rigorously proved recently. Therefore, it is expected that deaths caused by cancer can be substantially reduced through anti-cancer strategies which reduce the stemness of cancer cells.

The pathways by which cancer cells acquire stemness may be broadly summarized into two, one is the case where normal stem cells are transformed into cancer cells, and the other is the case where cancer cells acquire stemness through dedifferentiation. In patients with cancer, particularly, the key factors of embryonic stem cells play an important role in maintaining the stemness of cancer cells, and it was reported that the more malignant the cancer becomes, the more the expression of the embryonic stem cell-related gene group is increased rather than normal tissue stem cell-related genes. Three transcription factors, Oct4, Sox2, and Nanog, are central in a network that maintains the stemness of embryonic stem cells, and among them, OCT4 (gene Pou5f1) is known to play an important role in maintaining the stemness of cancer.

In the present invention, it was revealed that protein phosphatase 1 (PP1) induces the dephosphorylation of serine 236 (corresponding to serine 229 in a mouse) of human octamer-binding transcription factor 4 (OCT4) in human cells, and a peptide sequence inhibiting the functions of OCT4 and PP1 was identified. PP1 is a phosphatase having various substrates, and generally, PP1 inhibition also affects the functions of many proteins other than OCT4 to possibly cause various side effects, but the peptide of the present invention decreases stemness by specifically inhibiting the binding of PP1 and OCT4. It is expected that the peptide of the present invention may be used for reducing cancer and normal stemness by inducing the phosphorylation of OCT4, and particularly, suppressing the recurrence of cancer in a patient receiving anticancer treatment.

The OCT4 function-inhibiting peptide of the present invention inhibits the function of OCT4 by inhibiting the binding of OCT4 and PP1 to maintain the phosphorylation of serine 236 of human OCT4, thereby exhibiting the same level of effect as 100% deficiency of OCT4. For this reason, normal stem cells lose their stemness and differentiate, and cancer cells lose their stemness, thereby making long-term survival impossible and preventing recurrence after anticancer treatment. This is because the phosphorylation of serine 236 of OCT4 is maintained by a peptide which specifically inhibits the binding of OCT4 and a protein phosphatase PP1, and thus OCT4 fails to bind to DNA, resulting in a loss of transcriptional activity.

As used herein, the "stem cell" refers to a general concept of undifferentiated cells having the ability to differentiate into various types of tissue cells, that is, undifferentiated cells having stemness. These stem cells are roughly divided into embryonic stem cells which may be produced using embryos, adult stem cells, germ cells (gametes), cancer stem cells, and the like, the embryonic stem cells refer to a stage of a cell mass before foiling a specific organ and after fertilization, and recently, embryonic stem cells are also produced from normal cells through dedifferentiation. Therefore, the stem cells are not limited thereto as long as the stem cells are cells capable of differentiating into all cells and tissues constituting the body. Adult stem cells are extracted from umbilical cord blood, bone marrow, blood and the like, and refer to primitive cells just before differentiation into cells of specific organs such as bone, liver and blood. Germ cells are cells that transmit genetic information to the next generation through reproduction, and although human beings have sperm and ova, germ cells are not limited thereto. Cancer stem cells refers to cancer cells in a comprehensive sense, which have self-renewal or differentiation capabilities which are a unique ability of stem cells. Cancer stem cells generally may have resistance to anticancer agents by proliferating at a slow rate different from that of general cancer cells under normal tumor growth conditions (referring to a state where there is no cellular stress because the nutrients (glucose) necessary for cell growth are sufficient and the growth condition of the tumor microenviroment is abundant) or maintaining a dormant state, and for example, the expression of transcriptional regulatory factors such as PGC-la may be controlled unlike normal tumor cells, so that the functions of major metabolic regulators may differ from those of general cancer cells. Cancer stem cells comprehensively refer to cells with the ability to invade and metastasize, which have acquired resistance to cell apoptosis in a nutrient-deficient state through the regulation of a cell signal transduction system, which is mechanically linked with the different metabolic regulation abilities. However, cancer stem cells are not limited thereto as long as cancer stem cells are cells capable of differentiating into general cancer cells.

As used herein, the "prevention" refers to all actions that suppress a disease such as cancer or delay the onset of the disease by administering the composition according to the present invention.

As used herein, the "treatment" refers to all actions in which symptoms of a disease such as cancer are ameliorated or beneficially altered by administering the composition according to the present invention.

As used herein, the "individual" refers to a subject to which the composition of the present invention may be administered, and the subject is not limited.

In the present invention, the pharmaceutical composition may be in the form of a capsule, a tablet, a granule, an injection, an ointment, a powder, or a beverage, and the pharmaceutical composition may be characterized in that it is intended for humans. However, the pharmaceutical composition is not limited thereto and may be formulated into the form of an oral dosage form such as powder, granules, a capsule, a tablet, and an aqueous suspension, an external preparation, a suppository, and a sterile injectable solution. The pharmaceutical composition of the present invention may include a pharmaceutically acceptable carrier. As the pharmaceutically acceptable carrier, a binder, a lubricant, a disintegrant, an excipient, a solubilizing agent, a dispersing agent, a stabilizer, a suspending agent, a colorant, a flavoring agent, and the like may be used when orally administered, in the case of injection, a buffering agent, a preservative, an analgesic, a solubilizer, an isotonic agent, a stabilizer, and the like may be mixed and used, and in the case of topical administration, a base, an excipient, lubricant, a preservative, and the like may be used. The formulation of the pharmaceutical composition of the present invention may be variously prepared by mixing the pharmaceutical composition of the present invention with the pharmaceutically acceptable carrier as described above. For example, the formulation may be prepared in the form of a tablet, a troche, a capsule, an elixir, a suspension, a syrup, a wafer, and the like when orally administered, and in the case of an injection, the injection may be formulated into unit dosage ampoules or in multiple dosage forms. The pharmaceutical composition of the present invention may be formulated into other solutions, suspensions, tablets, capsules, sustained-release preparations, and the like.

Meanwhile, as an example of suitable carriers, excipients and diluents for formulation, it is possible to use lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil, or the like. Further, the pharmaceutical composition of the present invention may further include a filler, an anticoagulant, a lubricant, a wetting agent, a flavoring agent, an emulsifying agent, an antiseptic, and the like.

The route of administration of the pharmaceutical composition according to the present invention includes, but is not limited to, oral, intravenous, intramuscular, intraarterial, intramedullary, intrathecal, intracardiac, transdermal, subcutaneous, intraperitoneal, intranasal, enteral, topical, sublingual or rectal. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The pharmaceutical composition of the present invention may also be administered in the form of a suppository for rectal administration.

The pharmaceutical composition of the present invention varies depending on various factors including the activity of the specific compound used, age, body weight, general health, sex, diet, time of administration, route of administration, rate of excretion, drug combination and the severity of the particular disease to be prevented or treated, and the dosage of the pharmaceutical composition varies depending on the condition of the patient, the body weight, the degree of disease, the form of drug, the route of administration and duration, but may be appropriately selected by a person skilled in the art, and may be 0.0001 to 50 mg/kg or 0.001 to 50 mg/kg daily. The administration may be carried out once daily, and may be divided into several times. The dosage is not intended to limit the scope of the present invention in any way. The pharmaceutical composition according to the present invention may be formulated into pills, dragees, capsules, solutions, gels, syrups, slurries, and suspensions.

Hereinafter, the following Examples are suggested to aid in understanding the present invention. However, the following Examples are provided only to more easily understand the present invention, and the contents of the present invention are not limited by the following Examples.

EXAMPLES

Example 1: Confirmation of Link Between OCT4 Phosphorylation and Stemness 1.1. Construction of Cell Line Expressing Exogenous OCT4

In order to confirm the link between the phosphorylation of an octamer-binding transcription factor 4 (OCT4) protein and stemness, first, a cell line expressing OCT4 substituted with 236D as an OCT4 S236 phosphorylation mimetic mutant was constructed. For construction of cells, a lentivirus expressing short hairpin RNA (hRNA, SEQ ID NO: 1) and a puromycin resistance gene in a doxycycline-dependent manner was constructed, and primarily, NCCIT(ATCC® CRL-2073™) and NTERA-2 (ATCC® CRL-1973™), which are cancer stem cell lines, were transfected with the lentivirus. Then, a plasmid recombinant for expressing OCT4 wild type and blasticidine resistance genes, or OCT4 substituted with 236D which is a phosphorylation mimetic of OCT4 and blasticidine resistance genes in a pCAG-Flag-B/S vector was secondarily transfected into the transfected cell line using Lipofectamine 3000 (Thermo Fisher). Then, the cell line which was normally transfected and secondarily transfected was isolated by treating the medium with puromycin and blasticidine, and a cell line having the inhibited expression of endogenous OCT4 and substituted with an exogenous OCT4 protein was constructed by treating the isolated cell line with doxycycline. The constructed cell line was confirmed by western blotting. The cell line treated with doxycyline and cultured for 4 days to 8 days was washed using phosphate buffered saline (PBS), and after cells were lysed using a lysis buffer (20 mM Tris-Cl(pH 7.4), 150 mM NaCl, 1 mM EDTA, 1% (v/v) Triton X-100 and protease inhibitors), the cell lysis was confirmed by SDS-PAGE and western blotting using an OCT4 antibody (SantaCruz) and an Flag antibody (Cell Signaling). As a control, an ACTB antibody (Abcam) was used. The results are illustrated in FIG. 1.

As illustrated in FIG. 1, it was confirmed that the wild type OCT4 or the OCT4 substituted with 236D was normally transformed, and the exogenous OCT4 protein was expressed in a doxycycline-dependent manner.

Further, it was confirmed whether the exogenous OCT4 protein was expressed using immunofluorescence staining. For confirmation, after the cell line treated with doxycycline and cultured for 4 days to 8 days was washed using phosphate buffered saline, cells were fixed using a 4% formaldehyde solution, and then again treated with phosphate buffered saline, and treated with 0.5% Triton X-100 to enhance the permeability of the cell membrane. Then, the cells were blocked using a 1% bovine serum albumin (BSA) solution and treated with an OCT4 antibody to allow reaction at room temperature for 2 hours. Then, after the unbound antibody was removed with phosphate buffered saline, the cells were treated with a fluorescence-bound secondary antibody (Thermo Fisher Scientific) and reacted at room temperature for 1 hour, the unbound antibody was removed using phosphate buffered saline, and the nuclei were stained using 4',6-diamidino-2-phenylindole (DAPI, Calbiochem). Then, after a mounting solution was added onto the cells, it was confirmed whether a protein was expressed using a confocal microscope. The results are illustrated in FIG. 2.

Figure 2:
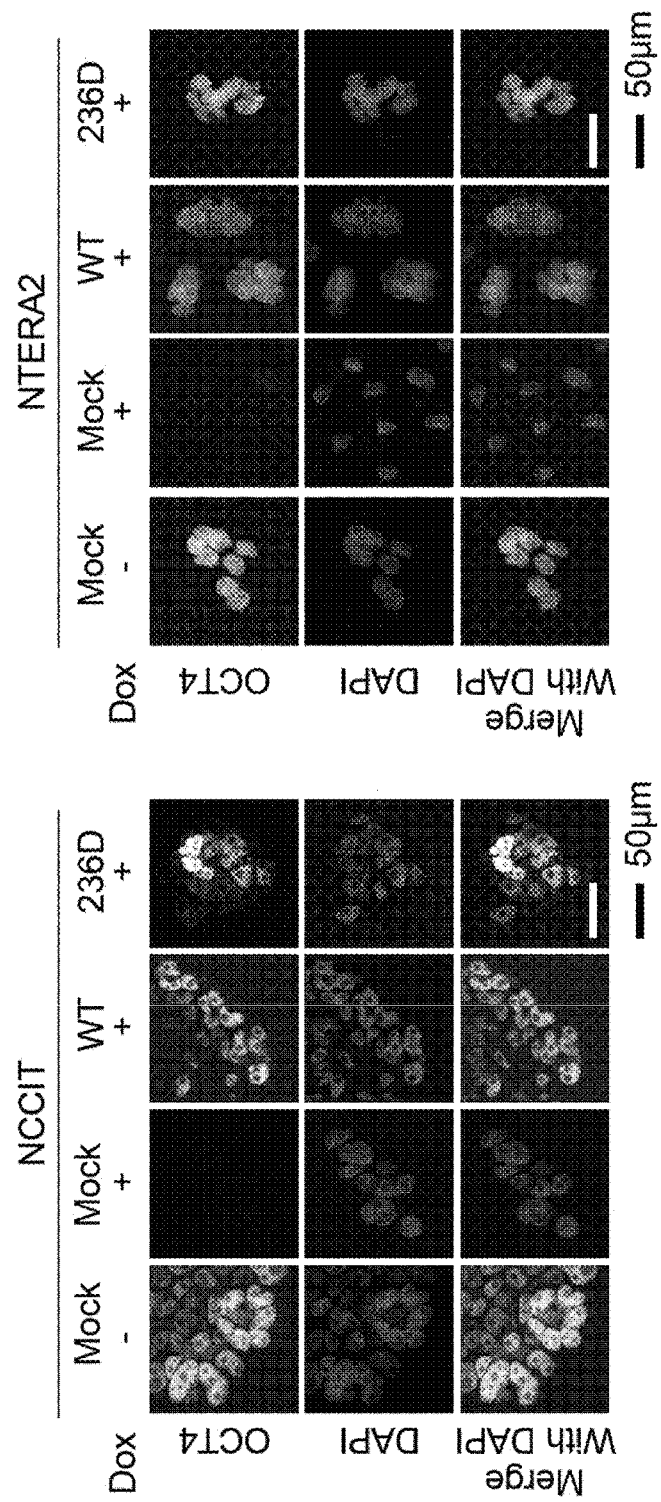
FIG. 2 is a view illustrating the results of confirming transformed cell lines according to an exemplary embodiment of the present invention using immunofluorescence staining.

As illustrated in FIG. 2, it was confirmed that the wild type OCT4 or the OCT4 substituted with 236D was normally transformed, and the exogenous OCT4 protein was expressed in a doxycycline-dependent manner.

1.2. Confirmation of Link Between OCT4 Phosphorylation and Stemness

In order to confirm the link between the OCT4 protein and stemness, after the cell line expressing the exogenous OCT4 constructed by the method in Example 1.1 was separated into single cells through trypsin treatment, 1,000 cells per well were aliquoted into 6-well plates and cultured under conditions of 37° C. and 5% $CO_2$ for a week or more, and then staining was performed using an alkaline phosphatase assay kit (Medsource Ozone Biomedicals) and observed using a microscope. The results are illustrated in FIG. 3.

Figure 3:
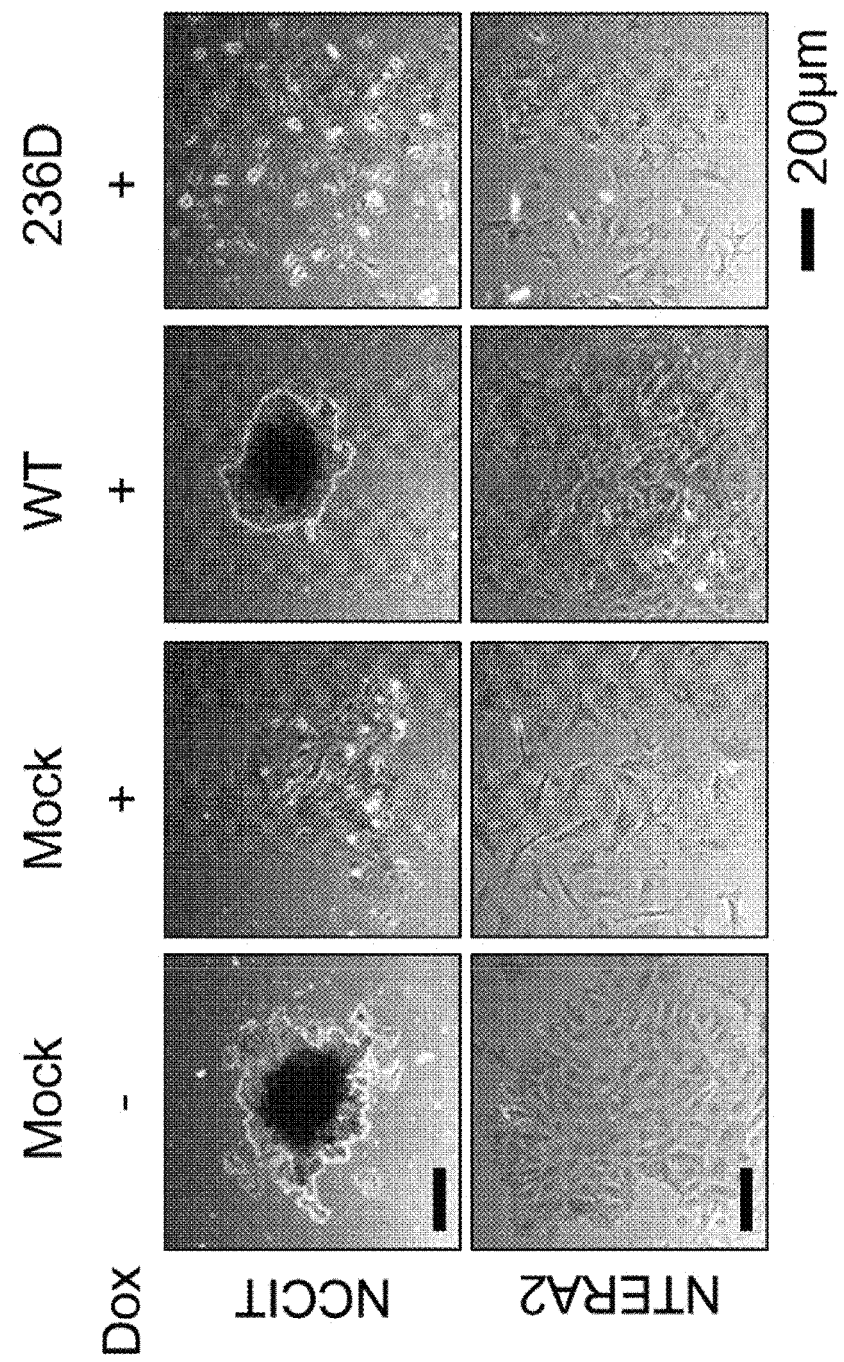
FIG. 3 is a view illustrating the results of confirming the stemness of transformed cell lines according to an exemplary embodiment of the present invention using alkaline phosphatase staining.

As illustrated in FIG. 3, it was confirmed that the cell expressing wild-type OCT4 maintained the same cell form as that of the control and maintained stemness, and thus showed a positive reaction to an alkaline phosphatase, whereas in the case of the cell expressing OCT4 substituted with 236D, the cells could not aggregate due to a variation in cell shape and showed a negative reaction to an alkaline phosphatase.

In addition, it was confirmed whether tumorspheres were formed. In order to form tumorspheres, 10,000 cells per well were aliquoted into 96-well Ultra Low Attachment plates (Corning) using a DMEM/F12 (Hyclone) medium supplemented with 1 mL of B27 (Invitrogen), 20 ng/mL epidermal growth factor (EGF, Sigma), 20 ng/ml basic fibroblast growth factor-2 (bFGF2, Sigma), and 4 ug/ml heparin (Sigma), and cultured under conditions of 37° C. and 5% $CO_2$ for two days, and then the same amount of medium was added thereto. Then, after 3 days, the cells were subcultured at a ratio of 1/10, and then cultured again for 7 days, the whole image of the 96-well was photographed by Cytation3 (BioTek), and spheroids having a diameter of 10 μm or more were counted. The results are illustrated in FIG. 4.

Figure 4:
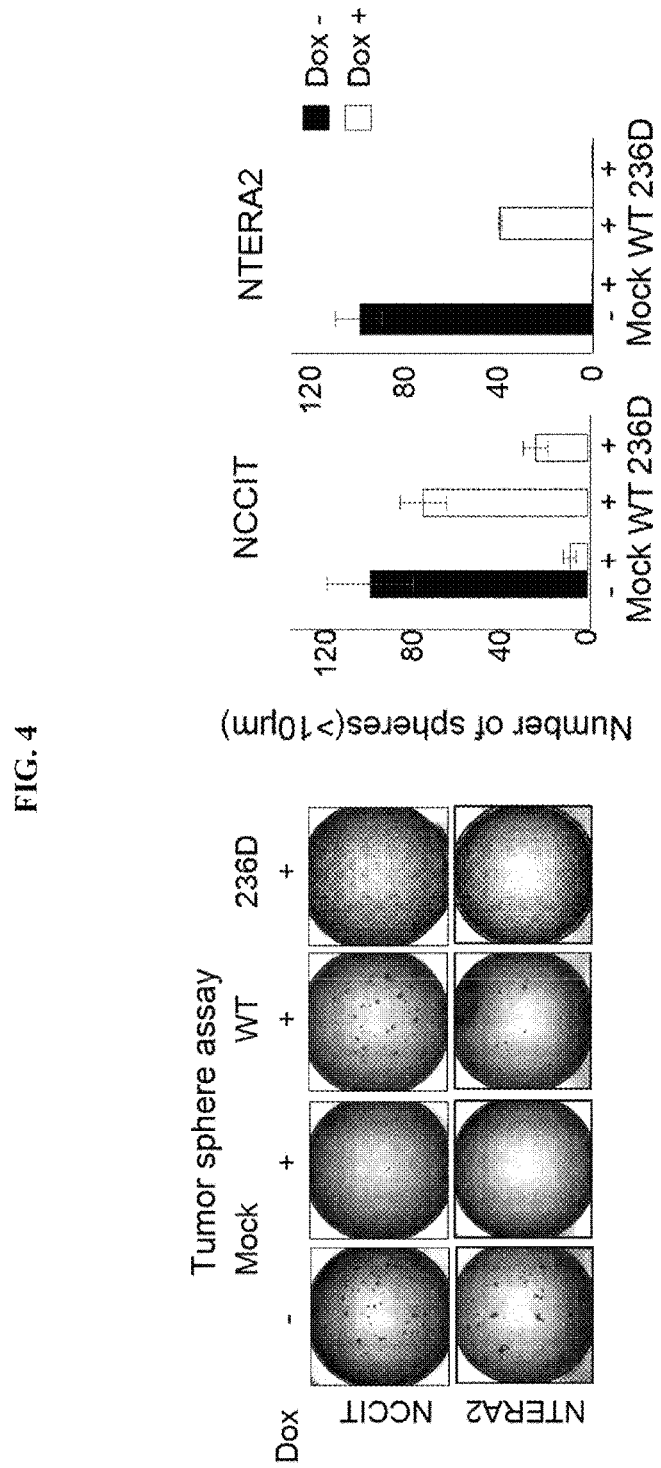
FIG. 4 is a view illustrating the results of confirming the stemness of transformed cell lines according to an exemplary embodiment of the present invention with the formation of tumorspheres.

As illustrated in FIG. 4, it was confirmed that in the case of the cell expressing OCT4 substituted with 236D, the formation of tumorspheres was remarkably reduced, and through this, it could be confirmed that in the case of OCT4 substituted with 236D, stemness was inhibited.

Further, after the total RNA from cells obtained by treating NCCIT cells expressing the exogenous OCT4 produced by the method in Example 1.1 with doxycycline and culturing the treated NCCIT cells and cells obtained by culturing the NCCIT cells without treatment was purified using an RNeasy purification kit (Qiagen), whole RNA-Seq was performed by commissioning Macrogen. The results are illustrated in FIG. 5.

Figure 5:
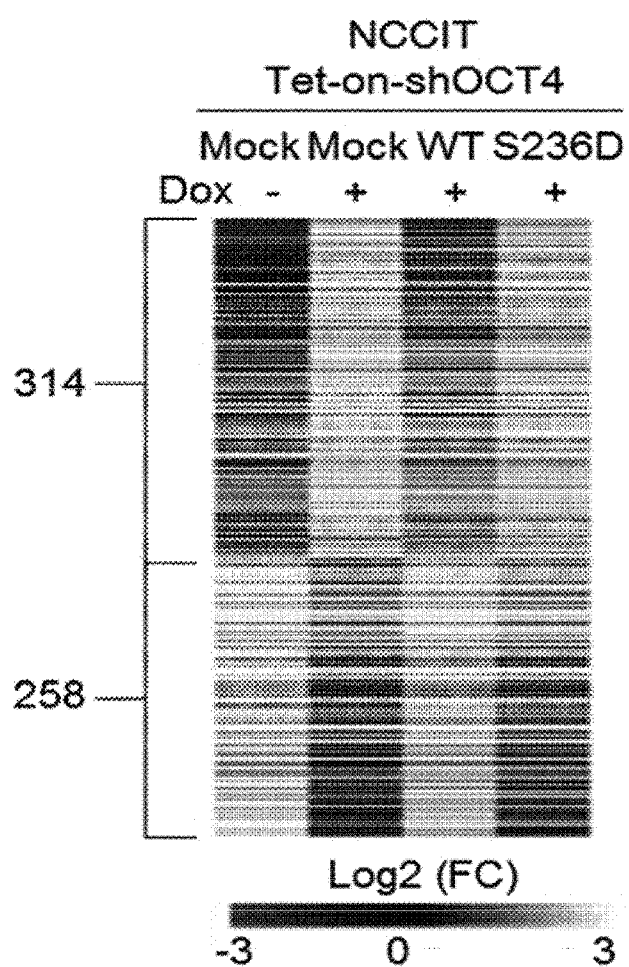
FIG. 5 is a view illustrating the result of comparing the gene expression patterns of transformed cell lines according to an exemplary embodiment of the present invention.

As illustrated in FIG. 5, it was confirmed that a transformed cell line expressing the wild-type OCT4 exhibited a gene expression pattern similar to that of an original cell line, and a transformed cell line expressing OCT4 substituted with 236D exhibited an expression pattern similar to that of a cell line from which OCT4 was removed.

Through the results, it could be confirmed that OCT4 plays an important role in maintaining stemness, and particularly when the phosphorylation of S236 was mimicked by substituting amino acid 236 of OCT4 with D, stemness was remarkably inhibited, and through this, the OCT4 S236 phosphorylation plays an important role in stemness.

Example 2: Confirmation of Link Between OCT4 Phosphorylation and Tumor Growth in Animal Model 2.1. Confirmation of Link Between OCT4 Phosphorylation and Tumor Growth $1 \times 10^7$ NTERA2 cells expressing the exogenous OCT4 constructed by the method in Example 1.1 were xenografted into BALB/c-nu mice, the mice were divided into two groups when the tumor size became about 50 to 100 $mm^3$, and the results of measuring the tumor size while administering doxycycline to one group and not administering doxycycline to the other group at 2- to 3-day intervals for 5 weeks are illustrated in FIG. 6.

Figure 6:
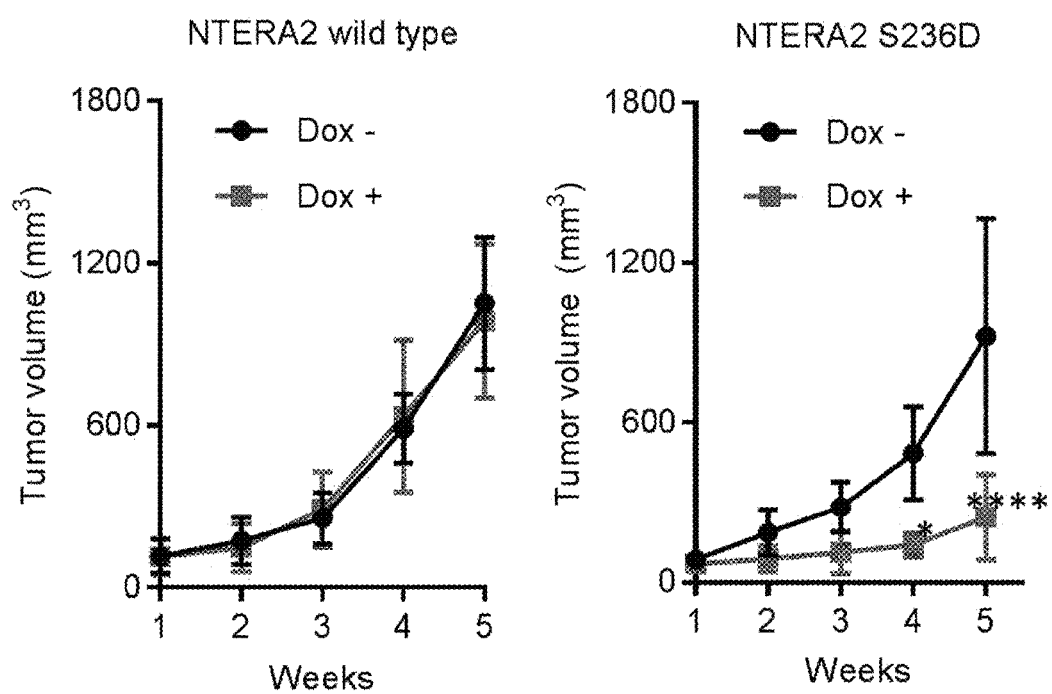
FIG. 6 is a view illustrating the results of comparing tumor growth curves using the mouse xenografts of transformed cell lines according to an exemplary embodiment of the present invention.

As illustrated in FIG. 6, it was confirmed that in the case of cells expressing OCT4 substituted with 236D, the growth of xenografted tumors was remarkably reduced.

Figure 7:
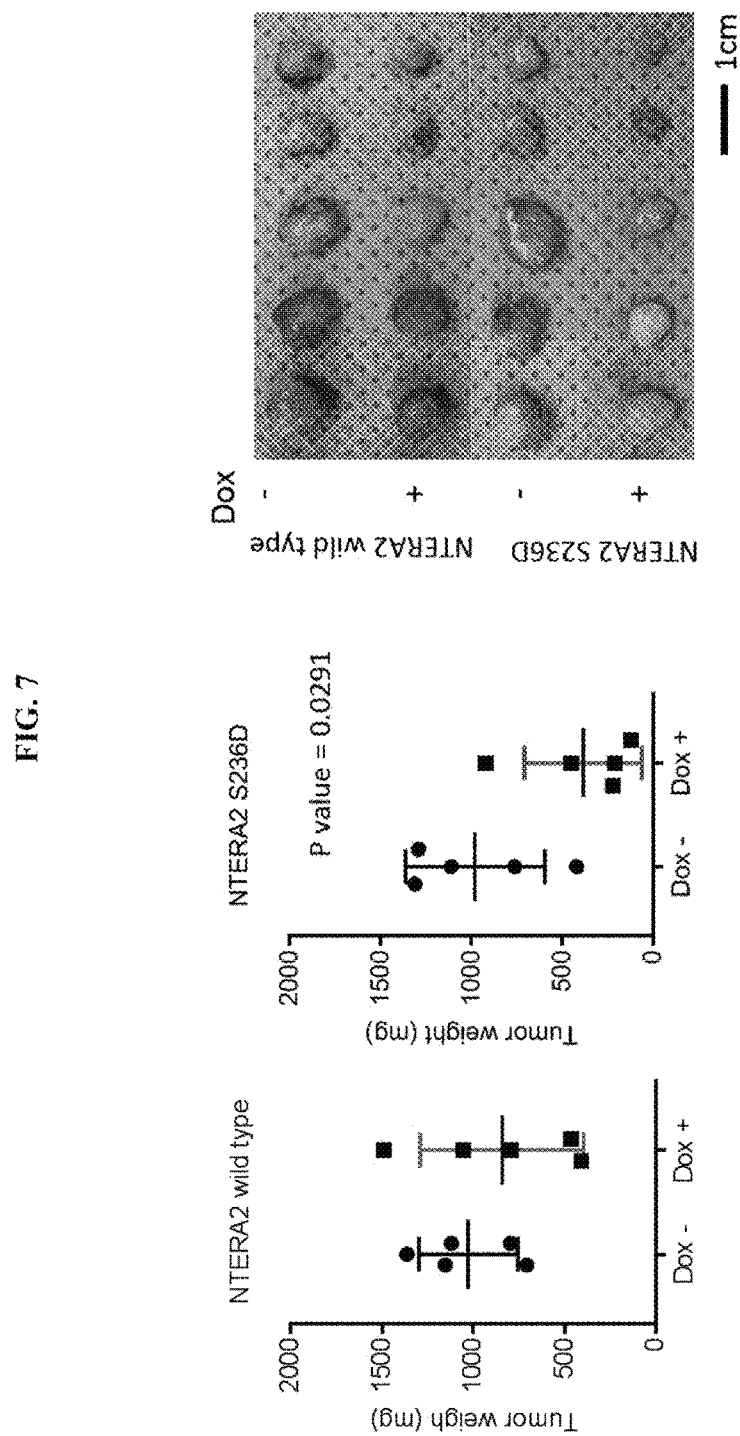
FIG. 7 is a view illustrating the results of comparing final tumor sizes using the mouse xenografts of transformed cell lines according to an exemplary embodiment of the present invention.

Further, after about 5 weeks, the tumor was detached from the mice, the tumor weight was measured and shown in a graph, and actual tumor images are illustrated in FIG. 7.

As illustrated in FIG. 7, it was confirmed that in the case of the cells expressing OCT4 substituted with 236D, the size of the xenografted tumor was remarkably small.

2.2. Confirmation of Link Between OCT4 Phosphorylation and Differentiation of Tumor Tissues After the tumor detached in Example 2.1 was fixed in formalin, paraffin blocks were prepared, and the results of staining with a growth marker Ki67 antibody using immunohistochemical staining are illustrated in FIG. 8.

Figure 8:
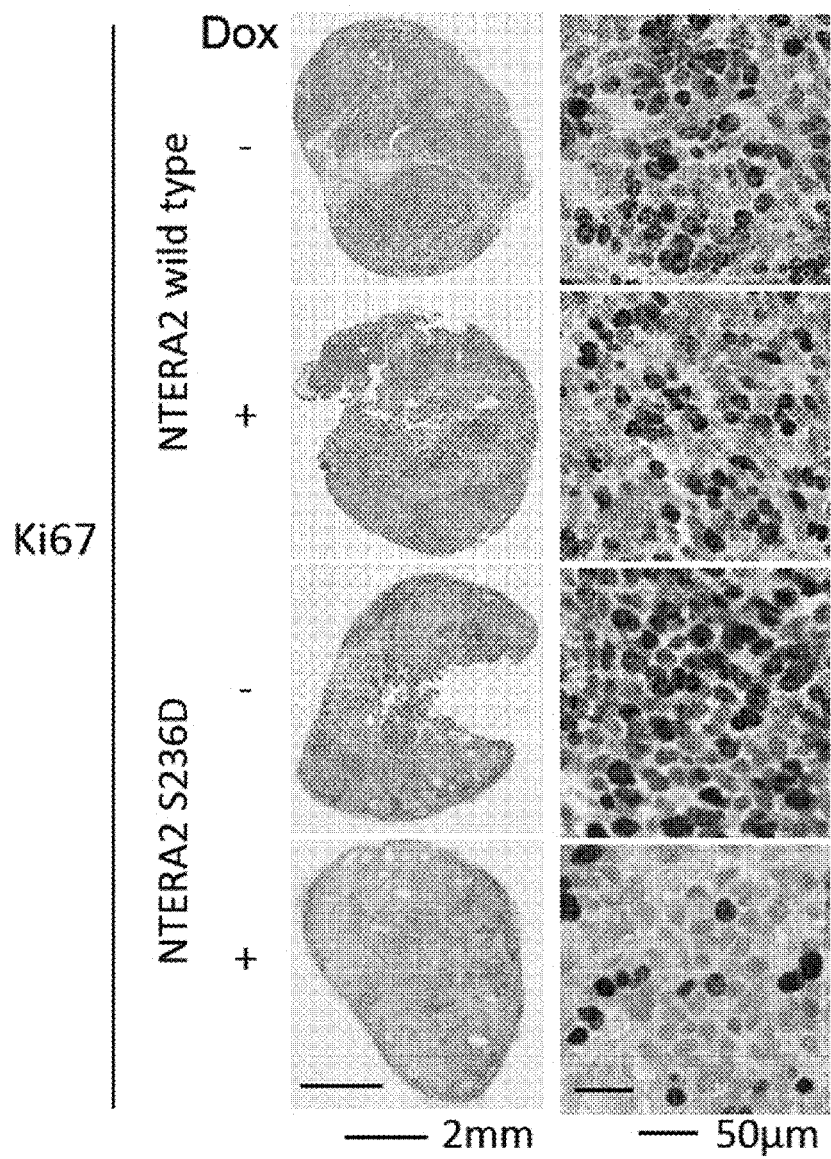
FIG. 8 is a view illustrating the results of comparing and confirming the degrees of staining using immunohistochemical staining in mouse xenograft tumors according to an exemplary embodiment of the present invention.

As illustrated in FIG. 8, it was confirmed that the Ki67 staining rate was remarkably low in the tumor tissue expressing OCT4 substituted with 236D.

Figure 9:
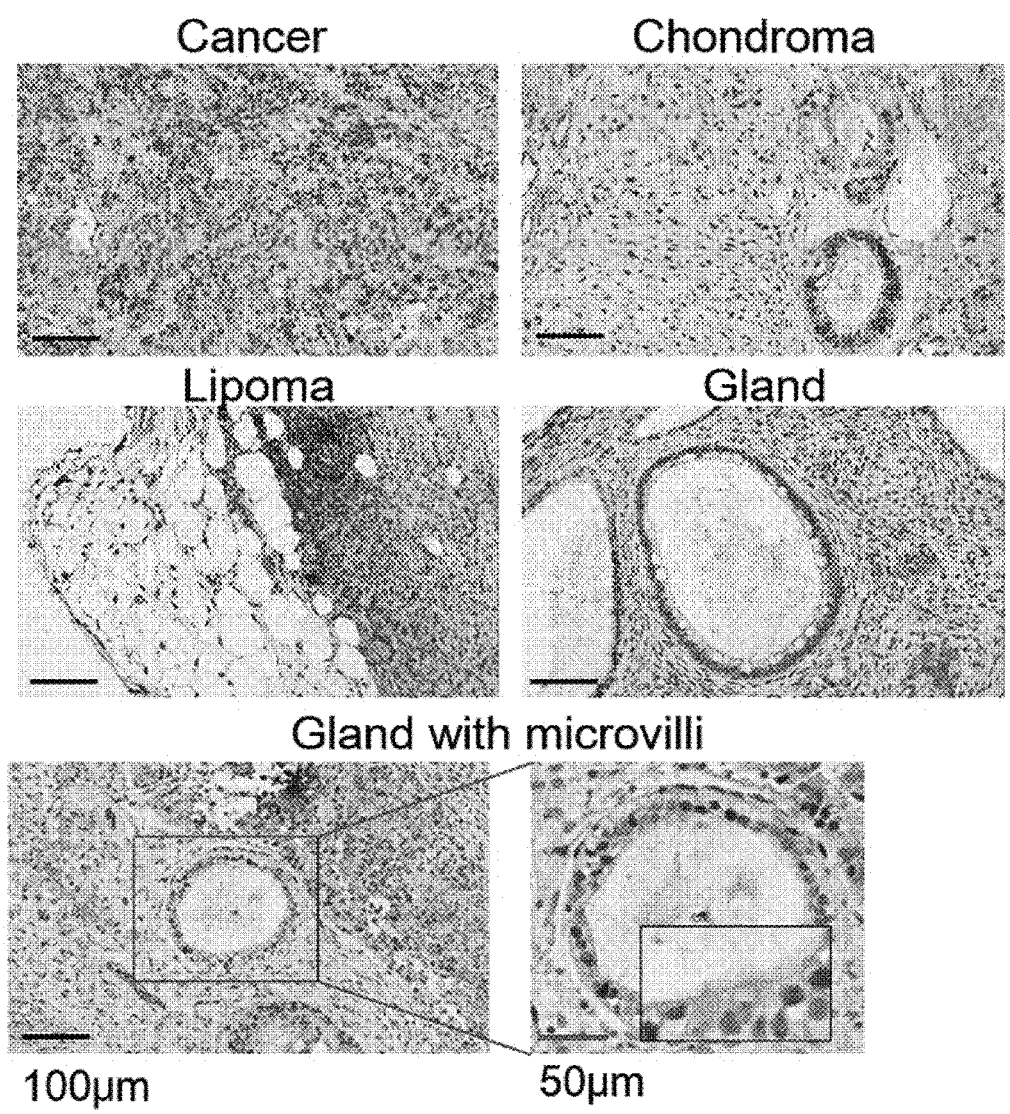
FIG. 9 is a view illustrating the results of confirming the differentiation of tissues using immunohistochemical staining in mouse xenograft tumors according to an exemplary embodiment of the present invention.

Further, the morphologies of the tumor tissue were enlarged and are illustrated in FIG. 9.

As illustrated in FIG. 9, in the tumor tissue expressing OCT4 substituted with 236D, a tissue having a tendency to lose stemness and differentiate into various morphologies was confirmed.

Example 3: Confirmation of Link Between PP1 and OCT4 Phosphorylation 3.1. Confirmation of Link Between PP1 and OCT4 Phosphorylation In order to confirm the link between protein phosphatase 1 (PP1) and OCT4, NCCIT and NTERA-2 cell lines were treated with okadaic acid known as an inhibitor of PP1, and western blotting and immunofluorescence staining were performed in the same manner as in Example 1.1. As the OCT4 S236 phosphorylation antibody, an antibody constructed by commissioning GenScript was used (ref. eLIFE2016). The results are illustrated in FIGS. 10 and 11, respectively.

Figure 10:
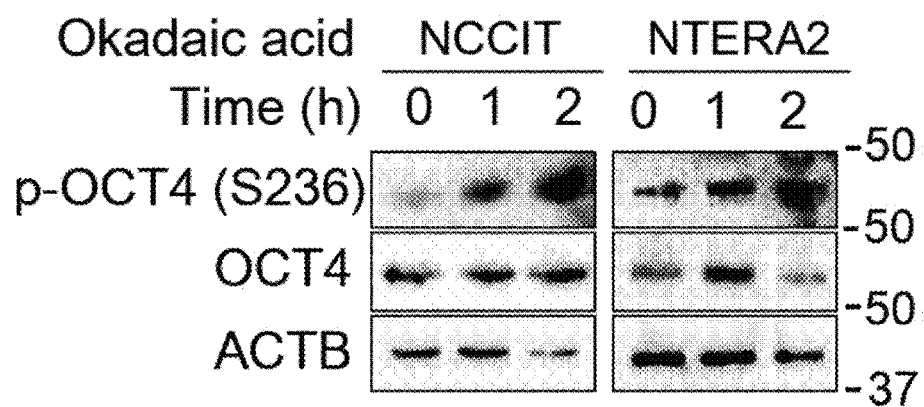
FIG. 10 is a view illustrating the results of confirming the association between PP1 according to an exemplary embodiment of the present invention and OCT4 S236 phosphorylation using western blotting.
Figure 11:
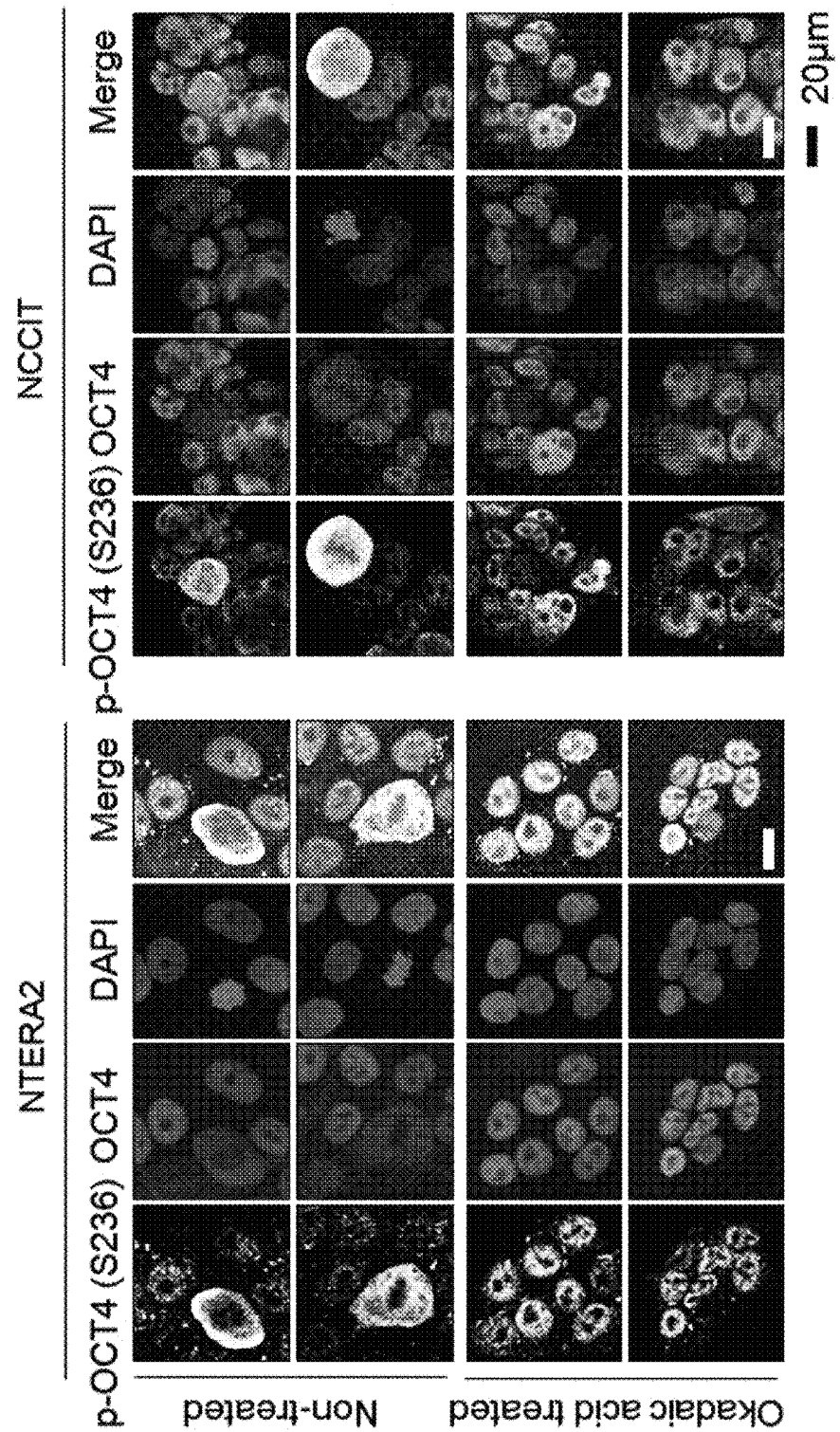
FIG. 11 is a view illustrating the results of confirming the association between PP1 according to an exemplary embodiment of the present invention and OCT4 S236 phosphorylation using immunofluorescence staining.

As illustrated in FIGS. 10 and 11, it was confirmed that when PP1 was inhibited, the phosphorylation of OCT4 was increased.

3.2. Construction of Cell Line for Regulating Inhibition of PP1 Expression

In addition, in order to construct a cell line for regulating the inhibition of PP1 expression, a cell line capable of regulating the expression of PP1 through doxycycline was constructed by constructing a lentivirus expressing shRNA of SEQ ID NO: 2 or 3 in a doxycycline-dependent manner and transfecting an NCCIT cell line with the lentivirus. Then, western blotting and immunofluorescence staining were performed in the same manner as in Example 2.1. The results are illustrated in FIGS. 12 and 13, respectively.

Figure 12:
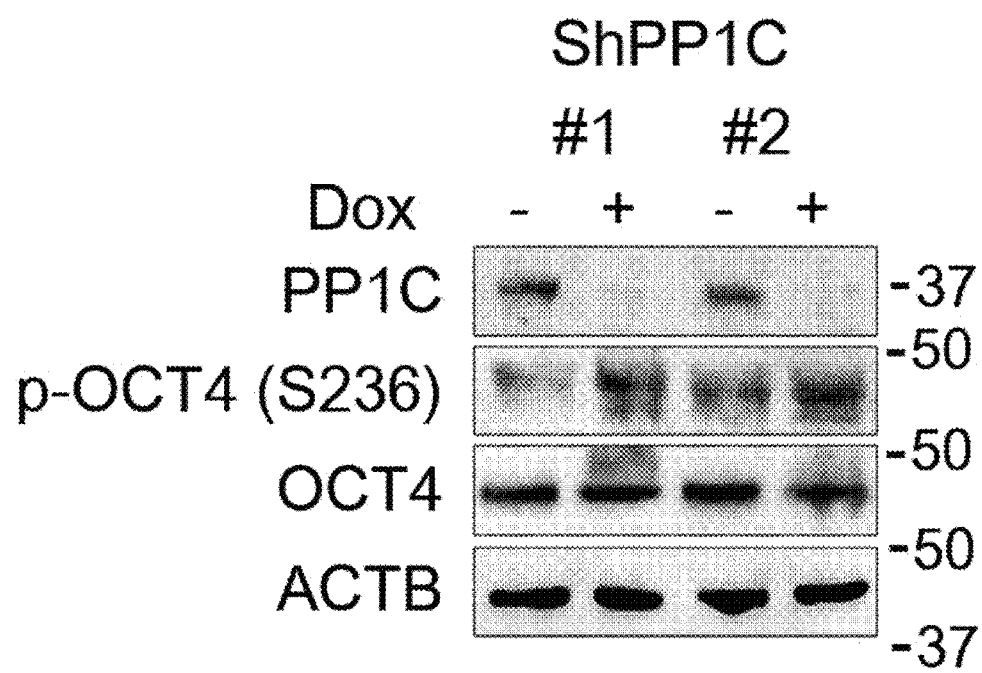
FIG. 12 is a view illustrating the results of confirming that the inhibition of expression of PP1 according to an exemplary embodiment of the present invention increases OCT4 S236 phosphorylation using western blotting.
Figure 13:
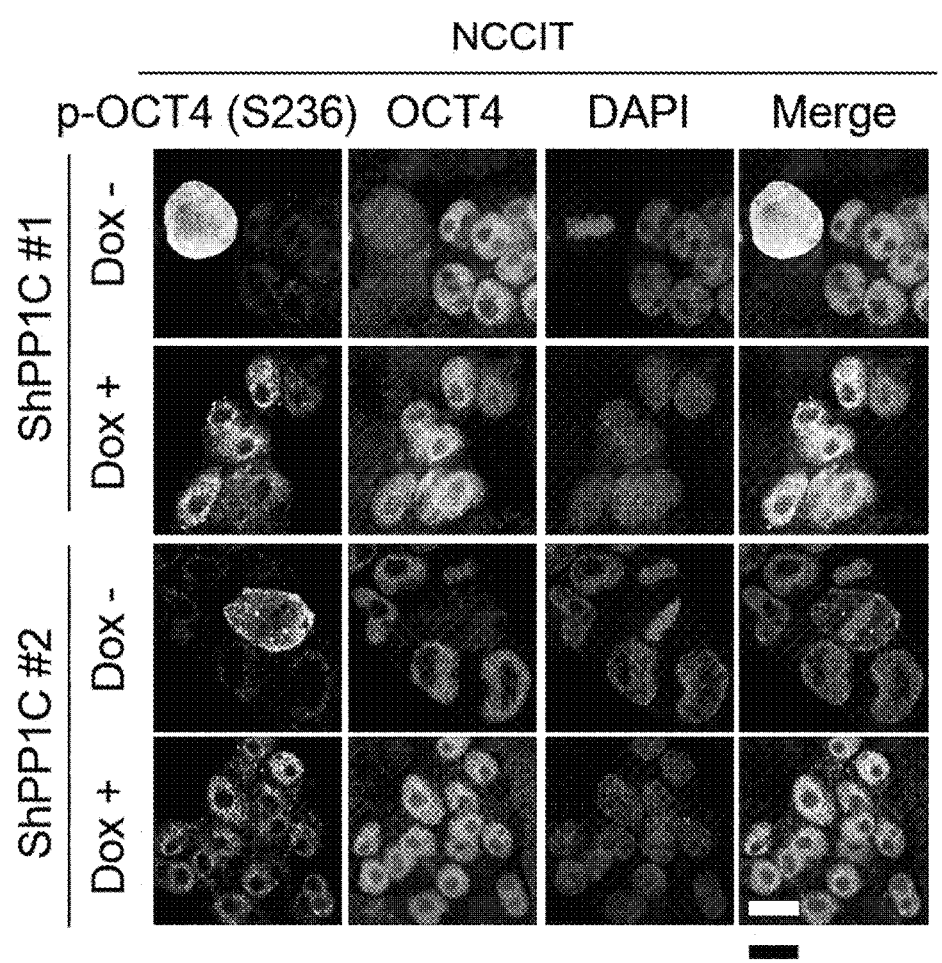
FIG. 13 is a view illustrating the results of confirming that the inhibition of expression of PP1 according to an exemplary embodiment of the present invention increases OCT4 S236 phosphorylation using immunofluorescence staining.

As illustrated in FIGS. 12 and 13, it was confirmed that when the expression of PP1 was suppressed using doxycycline, the phosphorylated OCT4 was increased.

3.3. Confirmation of Effects of Increase in OCT4 Phosphorylation Caused by PP1 Inhibition on Stemness In order to confirm effects of an increase in OCT4 phosphorylation caused by PP1 inhibition on stemness, alkaline phosphatase staining was performed and it was confirmed whether tumorspheres were formed in the same manner as in Example 1.2. The results are illustrated in FIG. 14.

Figure 14:
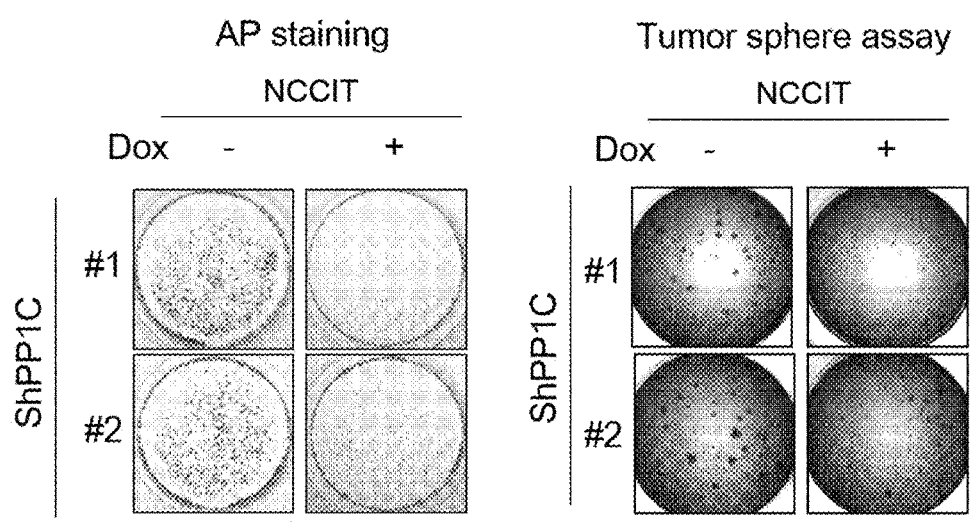
FIG. 14 is a view illustrating the results of confirming that the inhibition of expression of PP1 according to an exemplary embodiment of the present invention decreases stemness.

As illustrated in FIG. 14, it was confirmed that when the expression of PP1 was suppressed by doxycycline treatment, cells were not stained with an alkaline phosphatase, and the formation of tumorspheres was also remarkably reduced.

Through the result, it could be confirmed that when PP1 was suppressed, the phosphorylation of OCT4 was increased, thereby inhibiting stemness.

Example 4: Structural Analysis of OCT4

4.1. Prediction of Human OCT4 Structure

In order to predict the structure of human octamer-binding transcription factor 4 (OCT4), the structure of a site predicted to be involved in binding to PP1 was predicted using a mouse OCT4 X-ray crystal structure (PDBID:3L1P), whose partial structure is currently known, as a control. The results are illustrated in FIG. 15.

Figure 15:
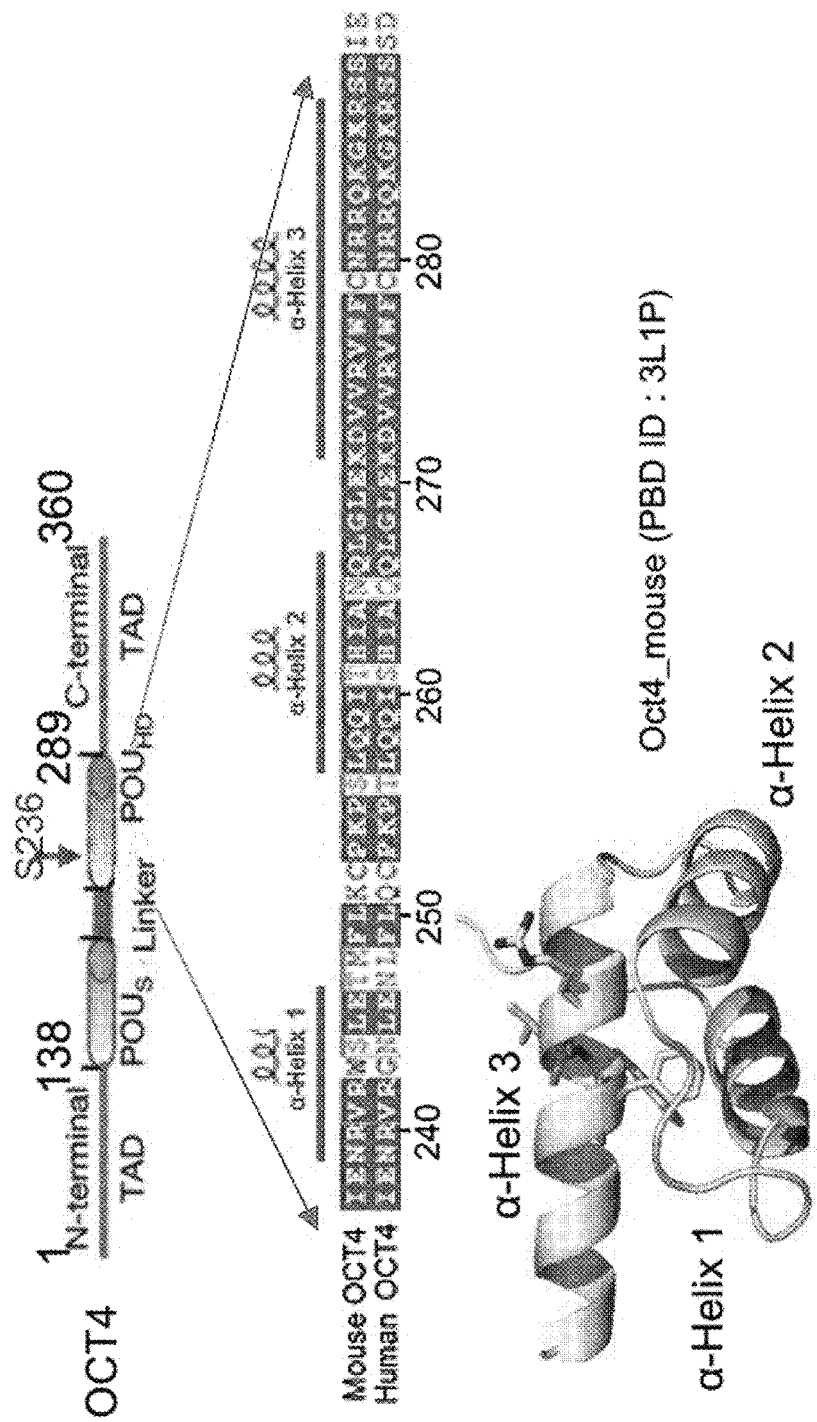
FIG. 15 is a view illustrating the results of predicting the 3D structure of an OCT4 protein according to an exemplary embodiment of the present invention. The mouse OCT4 sequence is described by SEQ ID NO: 16; and the human OCT4 sequence is described by SEQ ID NO: 17.

As illustrated in FIG. 15, in the case of the site predicted to be involved in binding to PP1, amino acid sequences of human OCT4 and mouse OCT4 are very similar to each other, and through this, it could be predicted that the structure of a human OCT4 protein at the corresponding site has a 3D (three dimensional) structure consisting of α-helix 1, α-helix 2, and α-helix 3.

Example 5: Construction of Peptide for Inhibiting Function of OCT4

Through the structural analysis of Example 4, base sequences of Helix 1-3 of SEQ ID NO: 4, Helix-1 of SEQ ID NO: 6, Helix-2 of SEQ ID NO: 8, and Helix-3 of SEQ ID NO: 10 were constructed in order to construct a peptide for inhibiting the function of OCT4 that is capable of inhibiting the function of OCT4 by reducing the binding between OCT4 and PP1. Then, a recombinant vector was constructed by inserting the constructed base sequences into a pCAG-F-puro vector (Addgene), respectively.

Example 6: Confirmation of Activity of Peptide for Inhibiting Function of OCT4

6.1. Confirmation of Stemness Inhibition Activity of Peptide for Inhibiting Function of OCT4

After an NCCIT cell line was transformed by inserting the vector constructed by the method in Example 5 into the NCCIT cell line using Lipofectamine 3000, and then cultured for 36 hours to 48 hours, western blotting was performed in the same manner as in Example 2.1. The quantification of western blotting was analyzed using ImageJ. The results are illustrated in FIG. 16.

Figure 16:
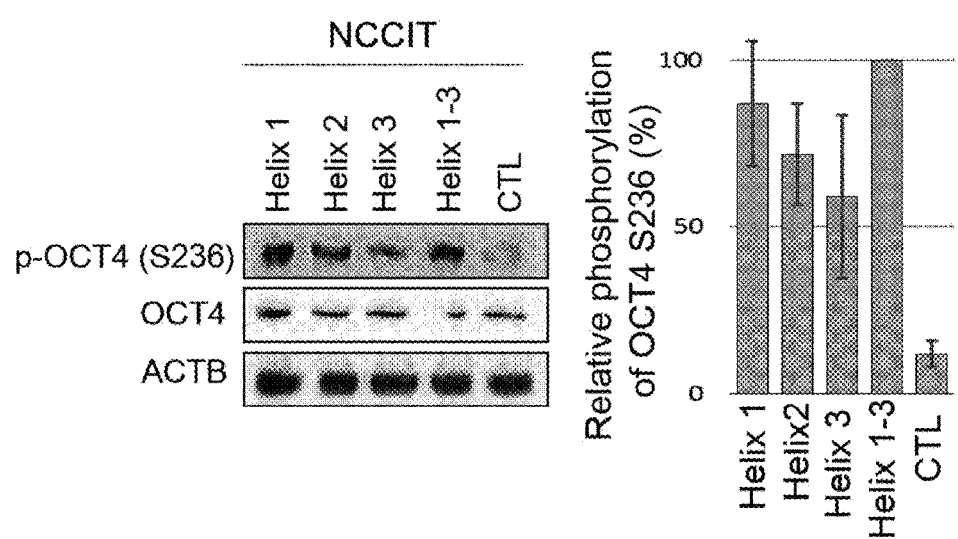
FIG. 16 is a view illustrating the results of confirming the activities of peptides for inhibiting the function of OCT4 of the present invention according to an exemplary embodiment of the present invention using western blotting.

As illustrated in FIG. 16, it was confirmed that all the peptides for inhibiting the function of OCT4 constructed by the method in Example 5 increased the phosphorylation of OCT4 in the NCCIT cell line, and particularly, the effects of Helix 1 and Helix 1-3 were the highest.

Figure 17:
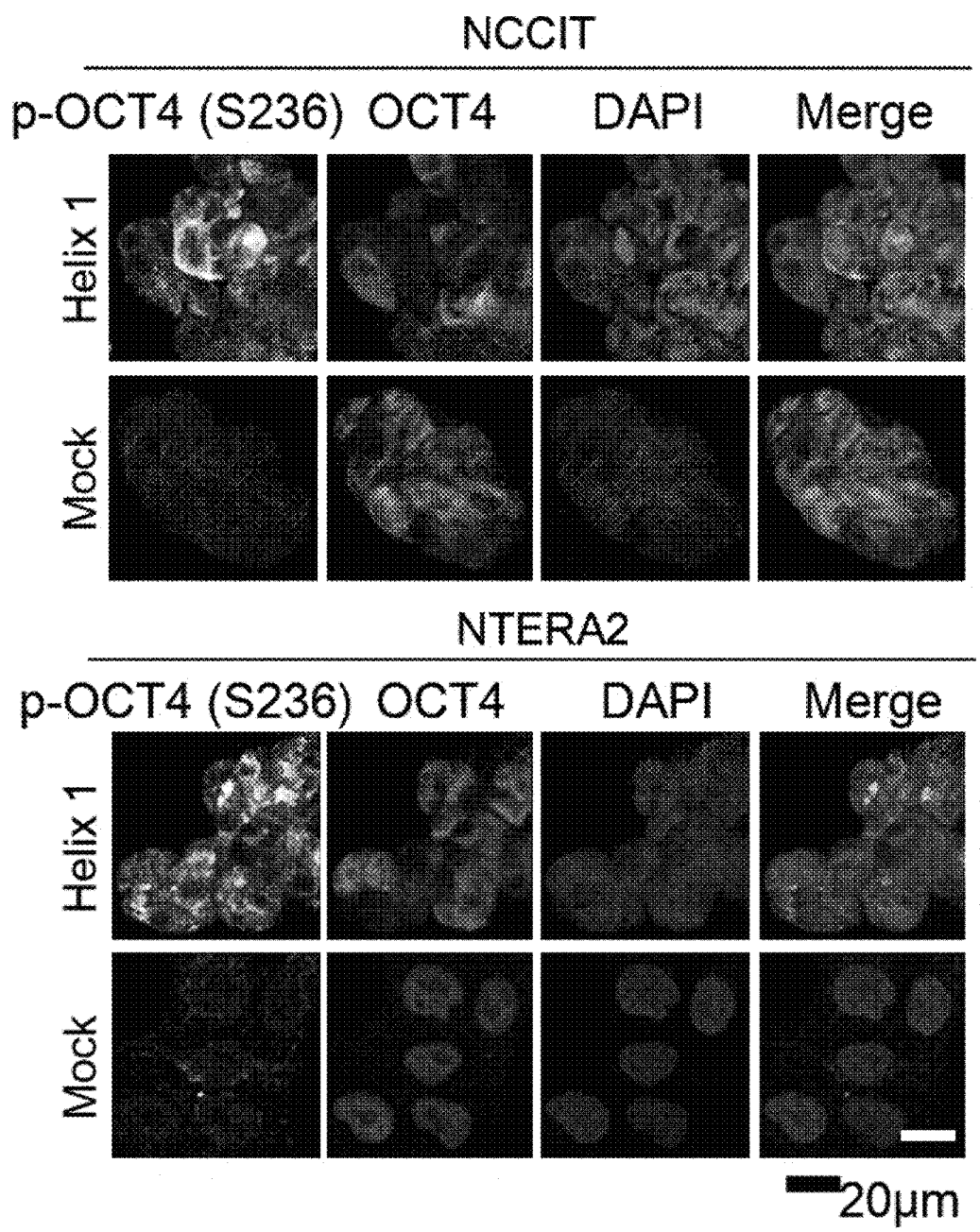
FIG. 17 is a view illustrating the results of confirming the activities of peptides for inhibiting the function of OCT4 of the present invention according to an exemplary embodiment of the present invention using immunofluorescence staining.

Furthermore, after NCCIT and NTERA-2 cell lines were transformed by inserting the vector constructed by the method in Example 5 into the NCCIT and NTERA-2 cell lines using Lipofectamine 3000, and then cultured for 36 hours to 48 hours, immunofluorescence staining was performed in the same manner as in Example 2.1, and the results are illustrated in FIG. 17.

In order to confirm whether stemness is reduced by an OCT4-PP1 binding inhibitory peptide, mouse embryonic stem cells (mESCs), NCCIT, and NTERA-2 cell lines were each transformed by the vector constructed by the method in Example 5 using Lipofectamine 3000, and then cultured for 2 days, treated with puromycin, and further cultured for 2 days to isolate only transformed cell lines into which a vector was inserted. Then, an alkaline phosphatase analysis was performed in the same manner as in Example 1.2 and a clonogenic assay of cancer cells was performed. The results are illustrated in FIG. 18.

Figure 18:
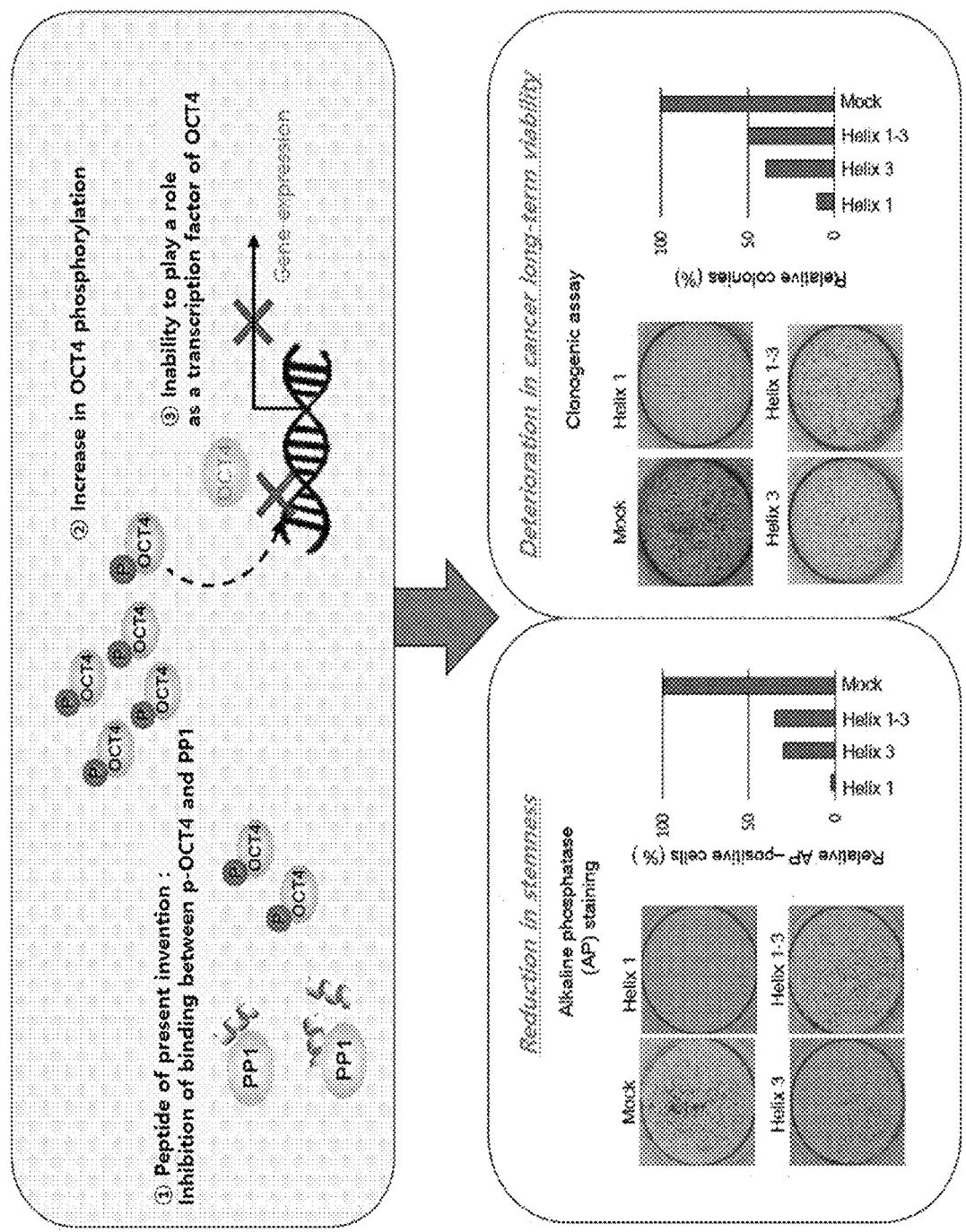
FIG. 18 is a view illustrating the results of confirming the stemness inhibition and cancer long-term viability reduction activities of the peptides for inhibiting the function of OCT4 of the present invention according to an exemplary embodiment of the present invention.

As illustrated in FIG. 18, it was confirmed that in the case of cells treated with a peptide for inhibiting the function of OCT4, cells did not aggregate due to a variation in cell morphology caused by a decrease in stemness, a negative reaction to an alkaline phosphatase was shown, and the viability of cancer cells was also reduced.

Peptides in which FITC was bound to Helix-1, Helix-2, and Helix-3 in Example 4 were synthesized.

Figure 19:
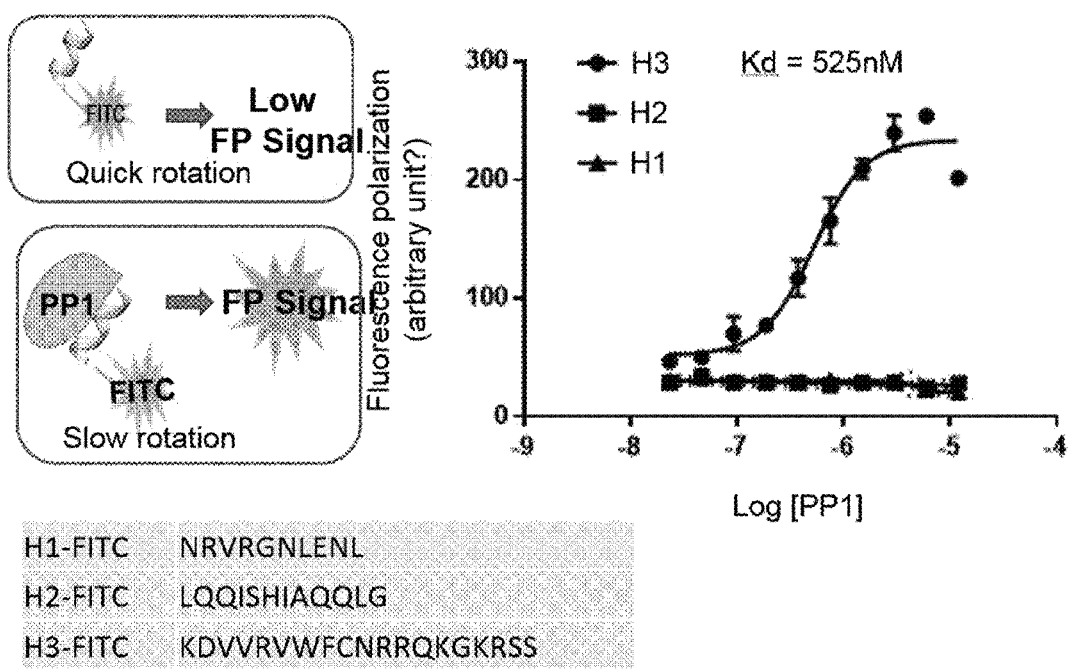
FIG. 19 is a view illustrating the results of confirming that the peptide for suppressing the function of OCT4 of the present invention according to an exemplary embodiment of the present invention binds to PP1 by fluorescence polarization. The three sequences depicted at the bottom of FIG. 19 are, respectively described by SEQ ID NO: 7 (H1-FITC), SEQ ID NO: 9 (H2-FITC) and SEQ IDNO 11 (H3-FITC).

The peptides were uniformly aliquoted at a final concentration of 20 nM into a fluorescence polarization reaction buffer solution (10 mM HEPES pH7.5, 50 mM NaCl, 1 mM DTT, 1 mM EDTA, and 0.0025% Tween 20), a purified PP1 protein was added thereto, and then the resulting mixture was reacted for 30 minutes, and the results of measuring fluorescence polarization using TECAN Infinite F200 Pro are illustrated in FIG. 19.

As illustrated in FIG. 19, it could be confirmed that when the PP1 protein was added, the fluorescence polarization values were remarkably increased, and thus, PP1 and the Helix 3 peptide were bound.

Figure 20:
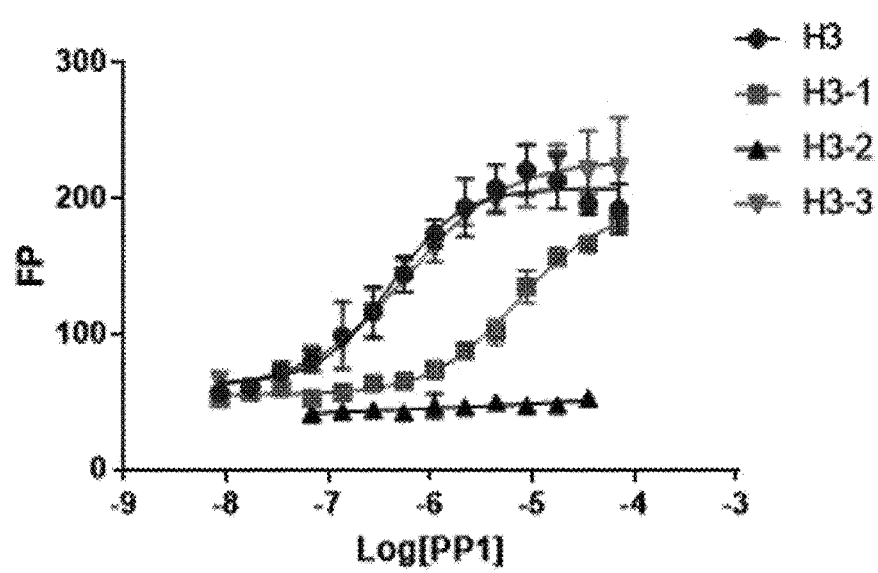
FIG. 20 is a view illustrating the results of confirming detailed sequences binding to PP1 in peptide sequences for inhibiting the function of OCT4 of the present invention according to an exemplary embodiment of the present invention by fluorescence polarization. The four sequences depicted at the bottom of FIG. 20 are, respectively described by SEQ ID NO: 11 (H3-FITC) SEQ ID NO: 14 (H3-1 FITC). SEQ ID NO: 15 (H3-2 FITC), and SEQ IDNO 13 (H3-3 FITC).

The binding powers of Helix 3-1 (SEQ ID NO: 14), Helix 3-2 (SEQ ID NO: 15), Helix 3-3 (SEQ ID NO: 13), and Helix 3 were compared by narrowing the sequence involved in binding to PP1 in the Helix-3 sequence (SEQ ID NO: 11)

consisting of 19 amino acids. As a result, finally, the results of showing that Helix 3-3 (SEQ ID NO: 13) consisting of 12 amino acids has the same binding power as that of Helix-3 are illustrated in FIG. 20.

Further, a cell permeable peptide (11R-GGG-VVRVWFCNRRQK: SEQ ID NO: 19) to which the sequence of Helix-3-3 was linked was constructed, and cells were treated with the cell permeable peptide for 2 days or more by adding the peptide at a concentration of 10 uM to a cell culture solution. The results of confirming an increase in phosphorylation of OCT4 after treatment by immunofluorescence staining are illustrated in FIG. 21.

In addition, an alkaline phosphatase analysis was performed in the same manner as in Example 1.2 and a clonogenic assay of cancer cells was performed. The results are illustrated in FIG. 22.

Figure 21:
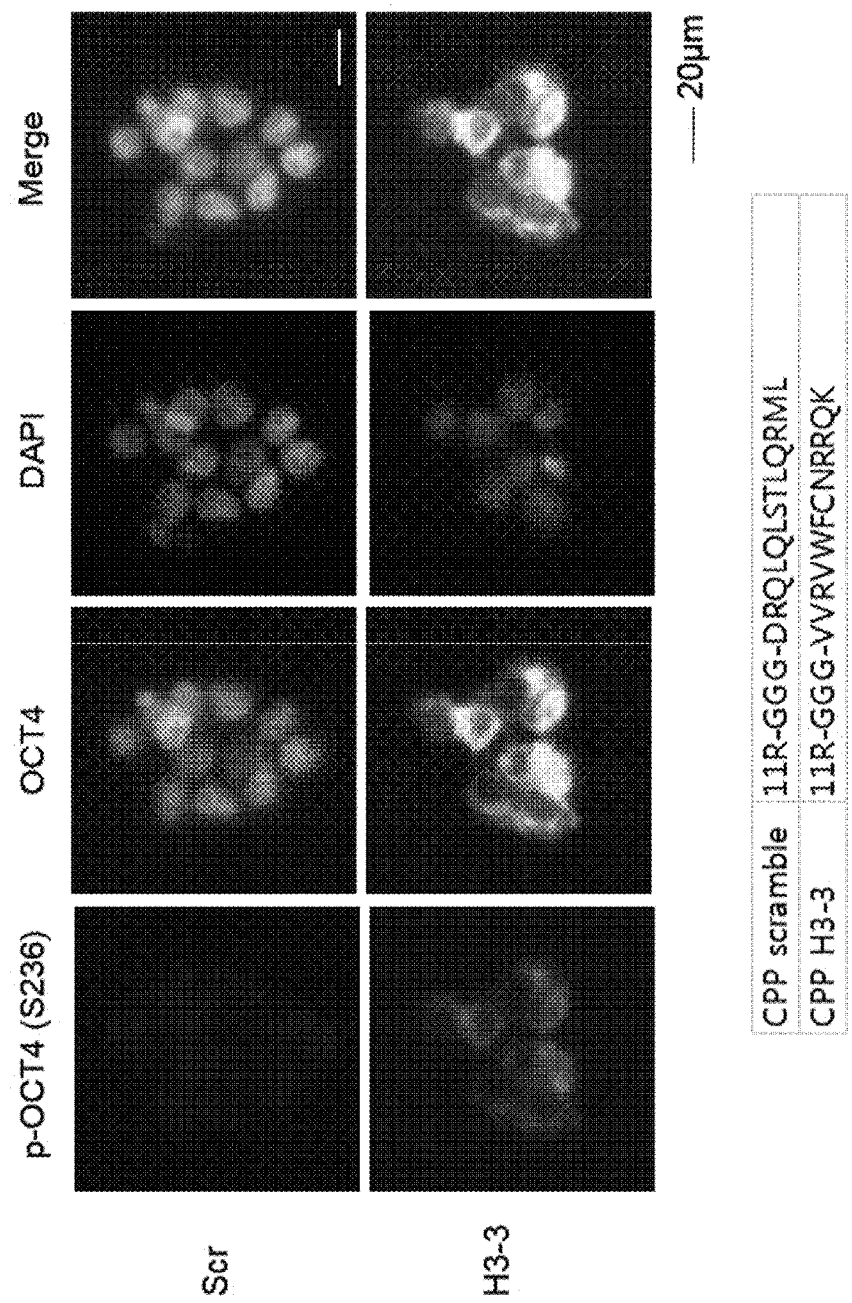
FIG. 21 is a view illustrating the results of confirming that the treatment of cell lines with a cell permeable peptide comprising the peptide sequence for suppressing the function of OCT4 of the present invention according to an exemplary embodiment of the present invention increases OCT4 S236 phosphorylation using immunofluorescence staining. The two sequences depicted at the bottom of FIG. 21 are, respectively described by SEQ ID NO: 18 (CPP scramble) and SEQ ID NO: 19 (CPP H3-3).
Figure 22:
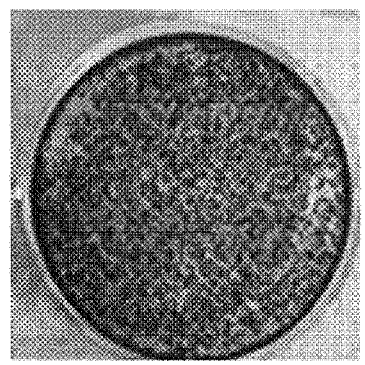
FIG. 22 is a view illustrating the results of confirming that the treatment of cell lines with a cell permeable peptide comprising the peptide sequence for suppressing the function of OCT4 of the present invention according to an exemplary embodiment of the present invention decreases stemness using alkaline phosphatase staining.
Figure 22:
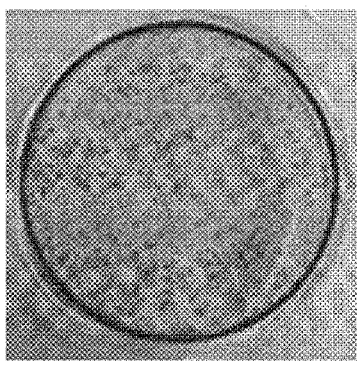
Figure 22:
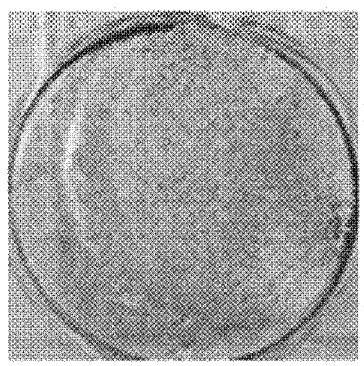
Figure 22:
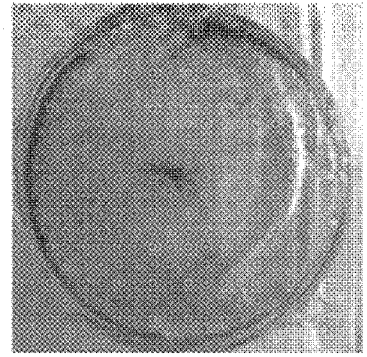
Figure 22:
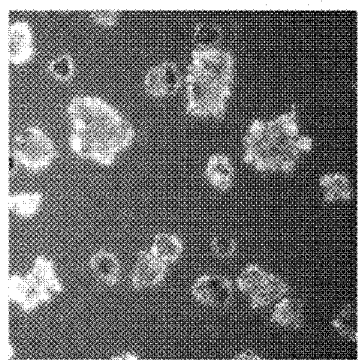
Figure 22:
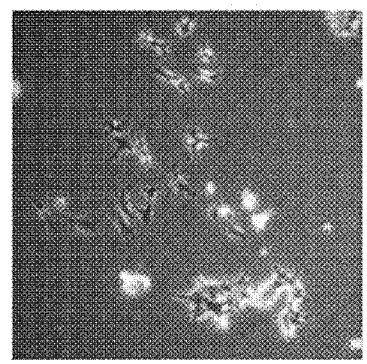

As illustrated in FIGS. 21 and 22, it was confirmed that in the case of cells treated with a peptide for inhibiting the function of OCT4, cells did not aggregate due to a variation in cell morphology caused by a decrease in stemness due to OCT4 phosphorylation, a negative reaction to an alkaline phosphatase was shown, and the viability of cancer cells was also reduced.

Through the results, it could be confirmed not only that the peptides for inhibiting the function of OCT4 of the present invention effectively suppressed the binding between OCT4 and PP1 to maintain the phosphorylation of serine 236 of human OCT4, prevented OCT4 from binding to DNA so that transcriptional activity was lost by inhibiting the function of OCT4, and could be effectively used in the suppression of cancer proliferation, suppression of cancer metastasis, suppression of cancer recurrence, suppression of occurrence of resistance of cancer to anticancer agents, and the like by finally reducing the stemness of cancer stem cells, but also that the peptides for inhibiting the function of OCT4 of the present invention can shorten the time and can enhance efficiency in the differentiation of embryonic stem cells into specific cells because it is possible to reduce stemness even in general stem cells, and the peptides for inhibiting the function of OCT4 of the present invention can find application in various fields by suppressing the stemness of stem cells because it is possible to effectively suppress side effects of oncogenesis caused by the remaining undifferentiated embryonic stem cells after cell therapy using embryonic stem cells.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

Since the peptides for suppressing the function of OCT4 according to the present invention can effectively reduce the stemness of various stem cells, the peptides can be effectively used for suppressing the proliferation of cancer, the recurrence of cancer, the metastasis of cancer, the occurrence of resistance of cancer to anticancer agents, and the like, and can also reduce the stemness of general stem cells, so that it is possible to shorten the time and enhance efficiency in the differentiation of embryonic stem cells into specific cells. Further, in cell therapy using embryonic stem cells, when the composition of the present invention is used, it is possible to completely remove undifferentiated embryonic stem cells remaining after treatment, and accordingly, it is possible to effectively suppress side effects of the occurrence of cancer, so that the stability of cell therapy using embryonic stem cells can be remarkably enhanced. Therefore, the value thereof is excellent in terms of industrial availability.

[Sequence Listing Free Text]

SEQ ID NO: 1: shRNA of OCT4
5'-TCATTCACTAAGGAAGGAATT-3'

SEQ ID NO: 2: shRNA #1 of PP1
5'-GCGAATTATGCGACCAACTGA-3'

SEQ ID NO: 3: shRNA #2 of PP1
5'-ACATTTGGTGCAGAAGTGGTTCT-3'

SEQ ID NO: 4: DNA sequence of Helix 1-3
AACCGAGTGAGAGGCAACCTGGAGAATTTGTTCCTGCAGTGCCCG
AAACCCACACTGCAGCAGATCAGCCACATCGCCCAGCAGCTTGGGCTGA
GAAGGATGTGGTCCGAGTGTGGTTCTGTAACCGGCGCCAGAAGGGCAAG
CGATCA SEQ ID NO: 5: Amino acid sequence of Helix 1-3
NRVRGNLENLFLQCPKPTLQQISHIAQQLGLEKDVVRVWFCNRRQKG
KRS SEQ ID NO: 6: DNA sequence of Helix 1
AACCGAGTGAGAGGCAACCTGGAGAATTTG SEQ ID NO: 7: Amino acid sequence of Helix 1
NRVRGNLENL SEQ ID NO: 8: DNA sequence of Helix 2
CTGCAGCAGATCAGCCACATCGCCCAGCAGCTTGGG SEQ ID NO: 9: Amino acid sequence of Helix 2
LQQISHIAQQLG SEQ ID NO: 10: DNA sequence of Helix 3
AAGGATGTGGTCCGAGTGTGGTTCTGTAACCGGCGCCAGAAGGGC
AAGCGATCA SEQ ID NO: 11: Amino acid sequence of Helix 3
KDVVRVWFCNRRQKGKRSS SEQ ID NO: 12: DNA sequence of Helix 3-3
GTGGTCCGAGTGTGGTTCTGTAACCGGCGCCAGAAGGGCAAG SEQ ID NO: 13: Amino acid sequence of Helix 3-3
VVRVWFCNRRQK SEQ ID NO: 14: Amino acid sequence of Helix 3-1
KDVVRVWFCN SEQ ID NO: 15: Amino acid sequence of Helix 3-2
CNRRQKGKRSS SEQ ID NO: 16: Amino acid sequence of Mouse OCT4
IENRVRWSLE TMFLKCPKPS LQQITHIANQ LGLEKDVVRV
WFCNRRQKGK RSSIE SEQ ID NO: 17: Ammo acid sequence of Human OCT4
IENRVRGNLE NLFLQCPKPT LQQISHIAQQ LGLEKDVVRV
WFCNRRQKGK RSSSD SEQ ID NO: 18: Amino acid sequence of Cell penetrating peptide CPP Scramble.
RRRRRRRRRR RGGGDRQLQL STLQRML SEQ ID NO: 19: Amino acid sequence of Cell penetrating peptide CPP H3-3
RRRRRRRRRR RGGGVVRVWF CNRRQK

The invention claimed is:

1. A method of treating cancer, the method comprising: administering to an individual in need thereof an effective amount of a peptide consisting of one amino acid sequence selected from the group consisting of SEQ ID NOS: 5, 7, 9, 11, and 13.

2. The method of claim 1, wherein the peptide suppresses the binding between octamer-binding transcription factor 4 (OCT4) and protein phosphatase 1 (PP1).

3. The method of claim 1, further comprising administering an anticancer agent.

4. The method of claim 1, wherein the method suppresses the proliferation of cancer, survival of cancer, metastasis of cancer, recurrence of cancer, or resistance of cancer to anticancer agents.

5. The method of claim 1, wherein the peptide is linked to a cell permeable peptide.

6. The method of claim 1, wherein the peptide is encoded by a polynucleotide comprising one base sequence selected from the group consisting of SEQ ID NOS: 4, 6, 8, 10, and 12.

* * * * *